(12) United States Patent
Huc et al.

(10) Patent No.: US 9,376,362 B2
(45) Date of Patent: *Jun. 28, 2016

(54) METHOD FOR THE HIGH-YIELD PRODUCTION OF P-(R-OXY)CALIX[9-20] ARENES

(71) Applicant: UNIVERSITE PARIS-SUD XI, Orsay (FR)

(72) Inventors: Vincent Germain Huc, Orsay (FR); Cyril Martini, Bures sur Yvette (FR)

(73) Assignee: UNIVERSITE PARIS-SUD XI, Orsay (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/424,135

(22) PCT Filed: Aug. 28, 2013

(86) PCT No.: PCT/FR2013/051988
§ 371 (c)(1),
(2) Date: Apr. 22, 2015

(87) PCT Pub. No.: WO2014/033406
PCT Pub. Date: Mar. 6, 2014

(65) Prior Publication Data
US 2015/0291494 A1    Oct. 15, 2015

(30) Foreign Application Priority Data

Aug. 28, 2012    (FR) ..................... 12 58052

(51) Int. Cl.
*C07C 43/23* (2006.01)
*C07C 41/30* (2006.01)
*C08G 8/08* (2006.01)

(52) U.S. Cl.
CPC ................. *C07C 43/23* (2013.01); *C07C 41/30* (2013.01); *C08G 8/08* (2013.01); *C07C 2103/90* (2013.01)

(58) Field of Classification Search
CPC .... C07C 43/23; C07C 41/30; C07C 2103/90; C08G 8/08
See application file for complete search history.

(56) References Cited

FOREIGN PATENT DOCUMENTS

| | | |
|---|---|---|
| CA | 2251070 A1 | 4/1996 |
| EP | 1361208 A1 | 11/2013 |
| FR | 2795077 A1 | 12/2000 |
| JP | 10260556 A | 9/1998 |

OTHER PUBLICATIONS

Yamagishi et al, Macromolecules, 2005, 38(16), 6871-75.*

C. David Gutsche et al., "Calixarenes. 4. The Synthesis, Characterization, and Properties of the Calixarenes from p-tert-Butylphenol," J. Am. Chem. Soc. 1981, 103, pp. 3782-3792.

Alessandro Casnati et al, (Benzyloxy)calix[8]arene: One-Pot Synthesis and Functionalization, The Journal of Organic Chemi Stry, vol. 62, No. 18, Sep. 1, 1997, pp. 6236-6239.

Vincent Huc et al: "C 3 V (Trimethyl) p-(Benzyloxy)calix[6]arene: A Versatile Platform for the Synthesis of Functionalized C 3 v Calix[6]arenes", European Journal of Organic Chemistry, vol. 2010, No. 11, Apr. 1, 2010, pp. 2199-2205.

C David Gutsche et al: "Calixarenes: paradoxes and paradigms in molecular baskets", Pure & Applied Chemistry, vol. 1. 62, No. 3, Jan. 1, 1990, pp. 485-491.

Ostaszewski R et al: "Influence of Base and Solvent on the Reaction between p-Cresol and Formaldehyde Leading to p-Methalcalix(n)arenes", Polish Journal of Chemistry, Polskie Towarzystwo Chemiczne, PL, vol. 1. 71, No. 8, Jan. 1, 1997, pp. 1053-1059.

Bernd Garska Macromolecular "Molecular Reinforcement Transparent Materials with Acrylamide-Modified Calix[4]arene as a Crosslinker", Macromolecular Materials and Engineering, va. 1. 297, No. 8, Feb. 10, 2012, pp. 785-789.

Nakayama T et al: "New Positive-Type Photoresist Based on Mono-Substituted Hydroquinone Calix (8) Arene and Diazonaphthoquinone", Journal of Materials Chemistry, Royal Society of Chemistry, GB, vol. 9, No. 3, Mar. 1, 1999, pp. 697-702.

Database Registry [Online], Chemical Abstracts Service, Columbus, Ohio, US; Apr. 26, 2004, XP002694618.

Database chemcats [Online], Chemical Abstracts Service, Columbus, Ohio, US; Aug. 21, 2012, XP002694619.

Roger Lamartine et al: Solid State Polycondensation of Precursors of Phenolic Resins II, Molecular Crystals and Liquid Crystals, vol. 134, No. I, Apr. 1, 1986, pp. 219-236, XP55058975.

Takeharu Haino et al: "Synthesis and binding behavior of an artificial receptor based on "upper rim" functionalized ca 1 i x [5] arene" , Tetrahedron, vo 1. 54, No. 40, Oct. 1, 1998, pp. 12185-12196, XP55058970.

Tyo Sone: "Inclusion Properties of Acyclic P-Substituted Phenol-Formaldehyde Oligomers", Bulletin of the Chemical Society of Japan, vo 1. 62, No. 4, Jan. 1, 1989, pp. 1111-1116.

Choi Sung-Seen: "Properties of butyl rubber vulcanizates cured by different type resoles", Polymer (Korea) Department of Chemical Engineering, Sogon University; Seoul, Korea, vol. 7, No. 3, Jan. 1, 1999, pp. 172-180.

Goodworth, Kerry J et al: "Synthesis and in vivo biological activity of large-ringed calixarenes against Mycobacterium tuberculosis", Tetrahedron, Elsevier Science Publishers, Amsterdam, NL, vo 1. 67, No. 2, Nov. 8, 2010, pp. 373-382, XP028165003.

International Search Report, for corresponding patent application, Nov. 11, 2013.

\* cited by examiner

*Primary Examiner* — Shailendra Kumar
(74) *Attorney, Agent, or Firm* — Young & Thompson

(57) ABSTRACT

A process for the high-yield preparation of p-(R-oxy)calix[9-20]arenes from a mixture of a base, a phenol, a source of formaldehyde and a organic solvent, p-(R-oxy)calix[9-20] arenes obtained from such a process, and uses of such p-(R-oxy)calix[9-20]arenes.

26 Claims, 22 Drawing Sheets

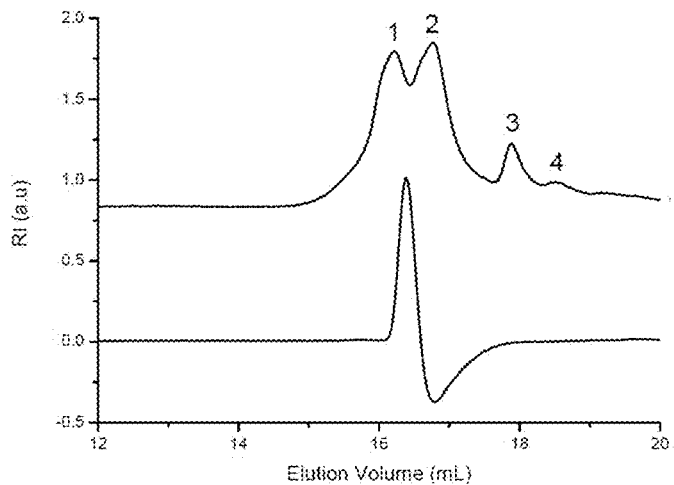
Figure 4.1 : Fraction F0
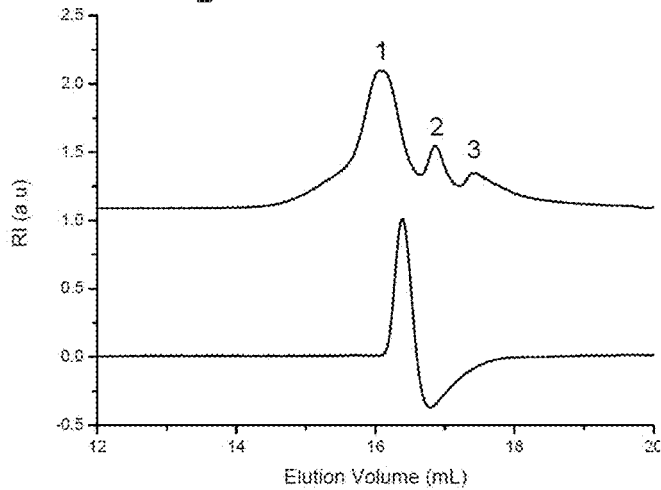
Figure 4.2 : Fraction P3
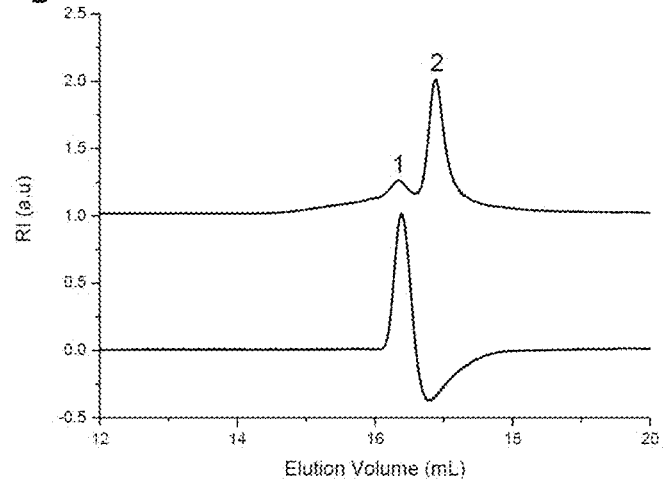
Figure 4.3 : Fraction F5

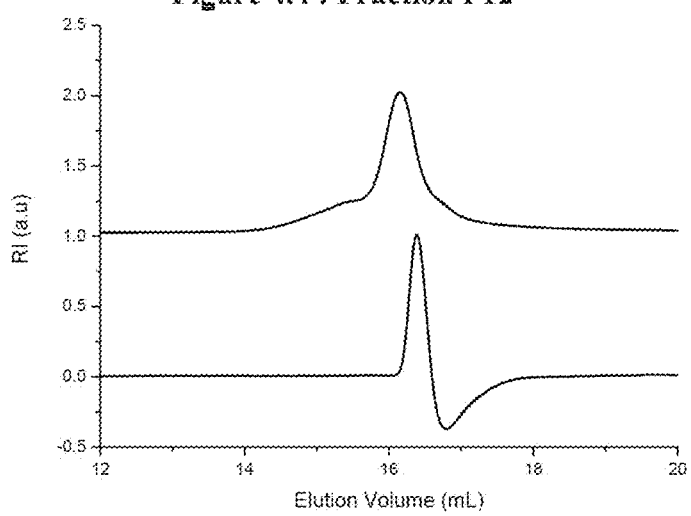
Figure 4.4 : Fraction P12
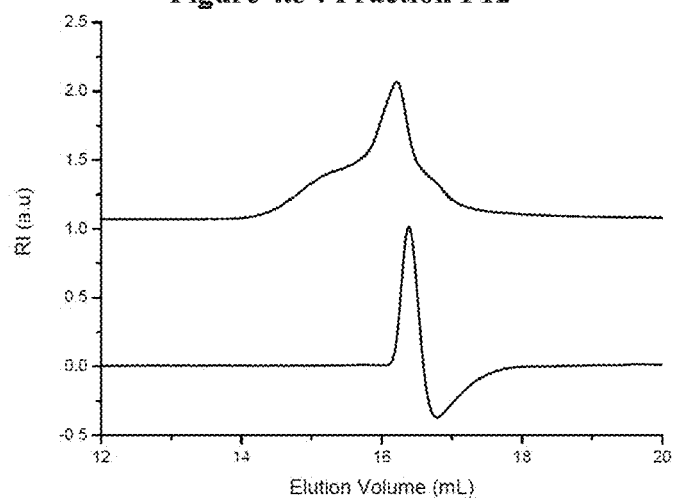
Figure 4.5 : Fraction F12
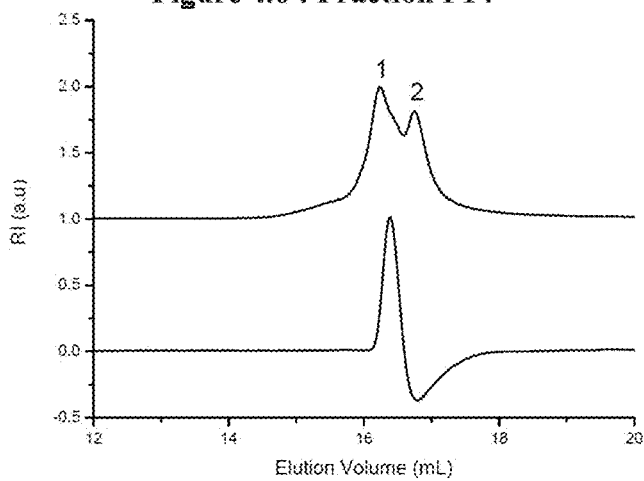
Figure 4.6 : Fraction P14

Figure 4.7 : Fraction F14
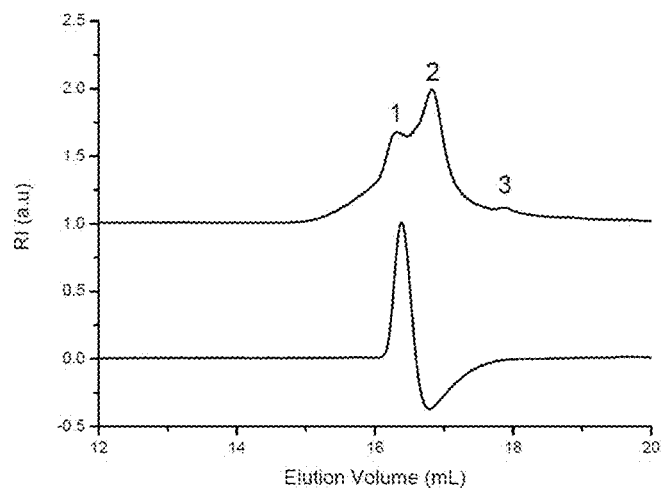
Figure 4.8 : Fraction P15
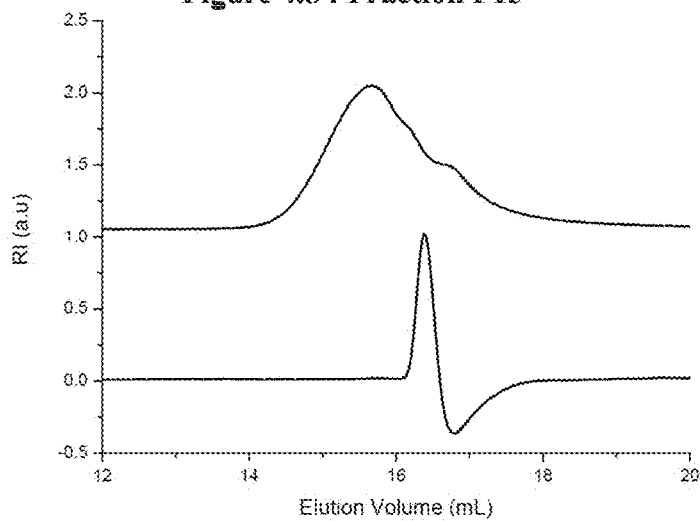
Figure 4.9 : Fraction P16
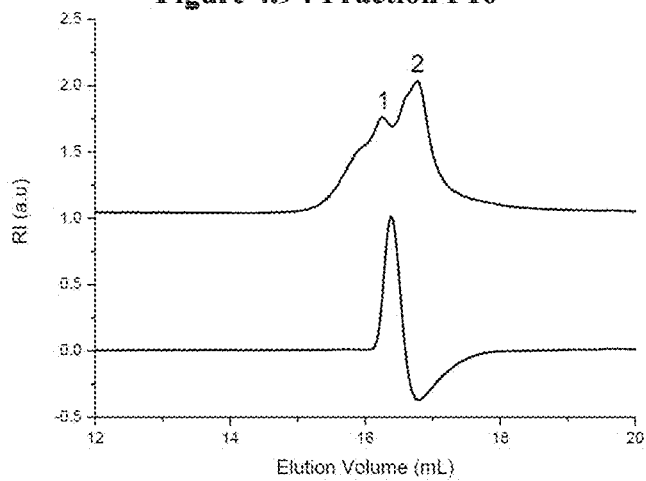

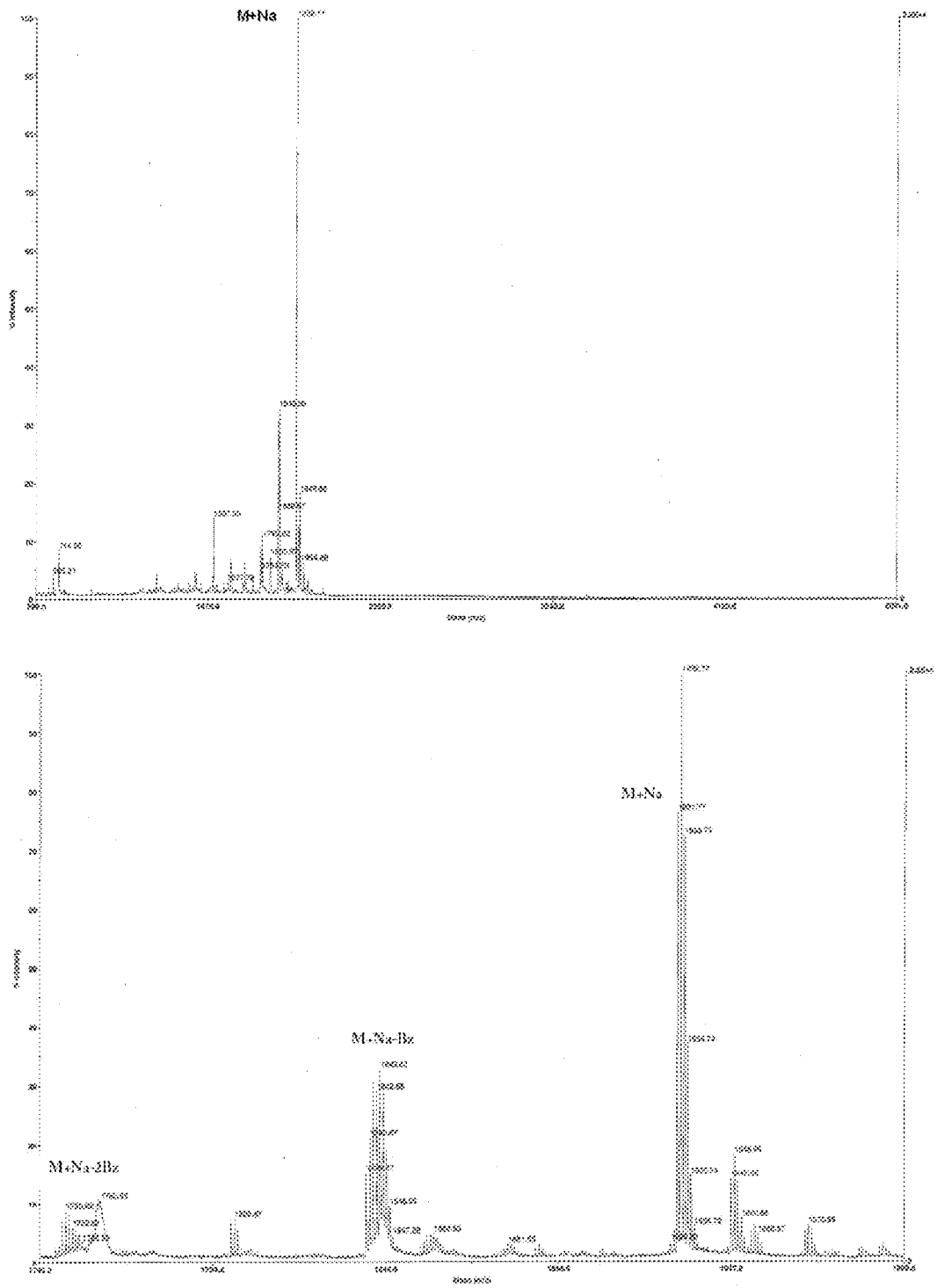

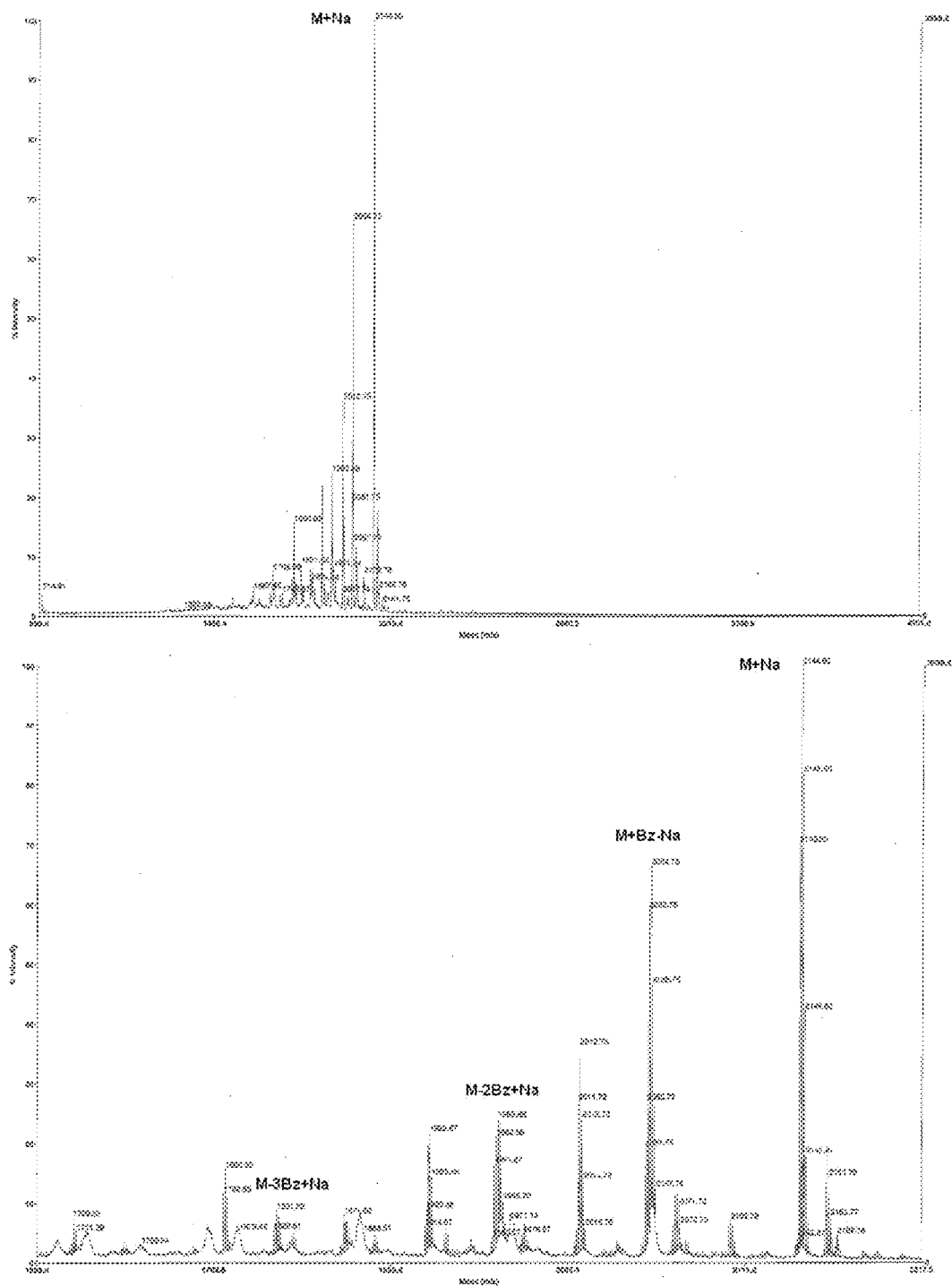
Figure 5.2 : Fraction P7 (Calix[10]arene)

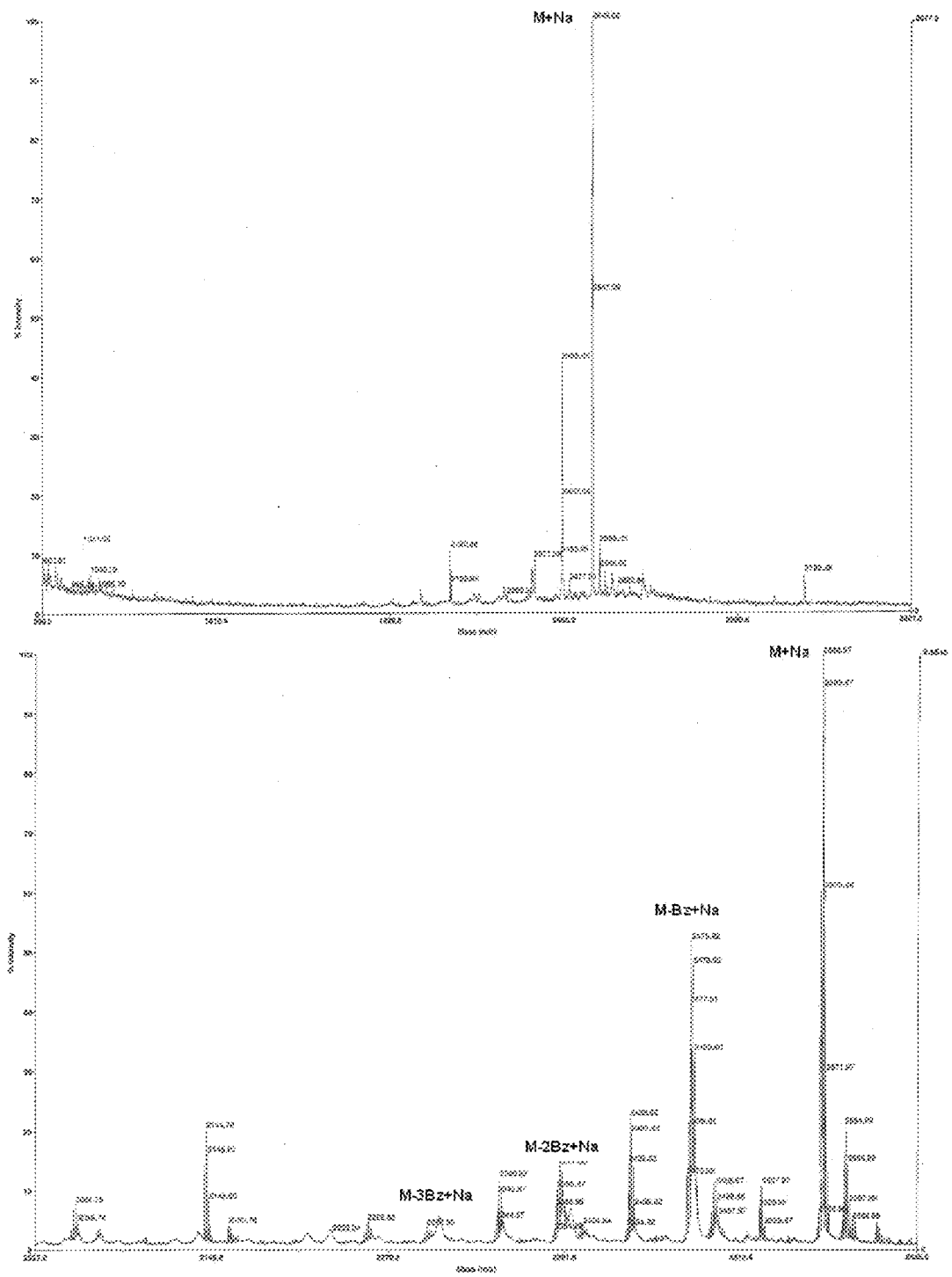
Figure 5.3 : Fraction P10 (Calix[12]arene)

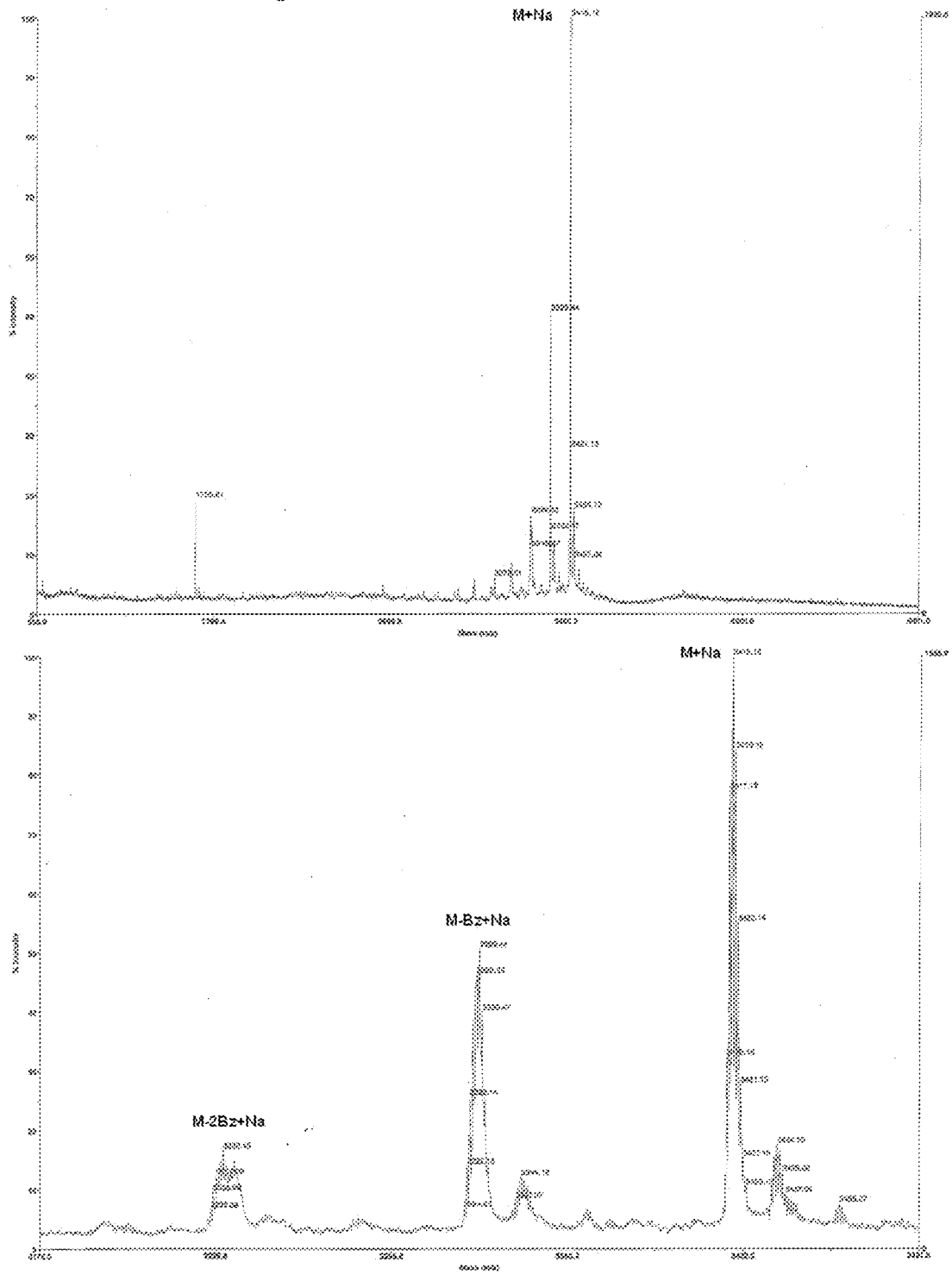
Figure 5.4 : Fraction P4 (calix[16]arene)

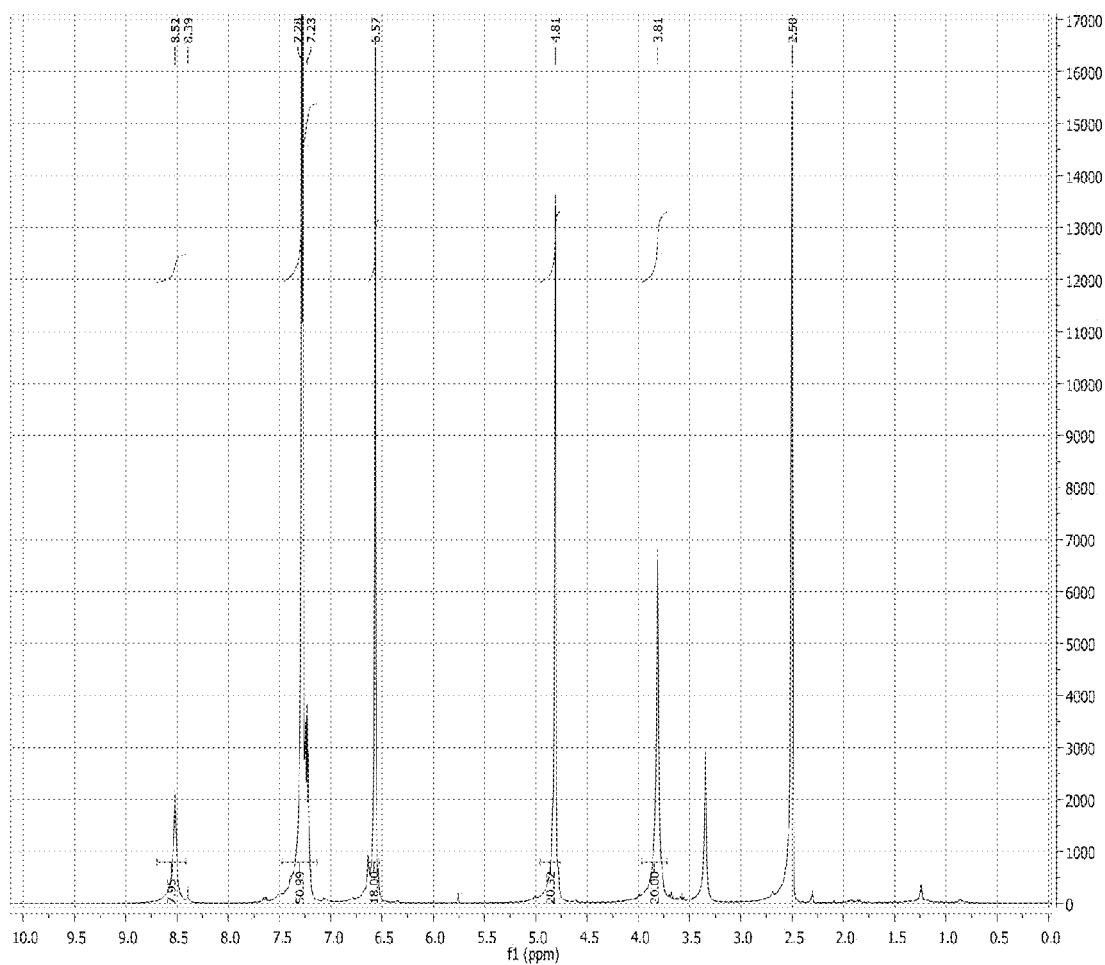
Figure 6.1 : Fraction F6b (Calix[9]arene)

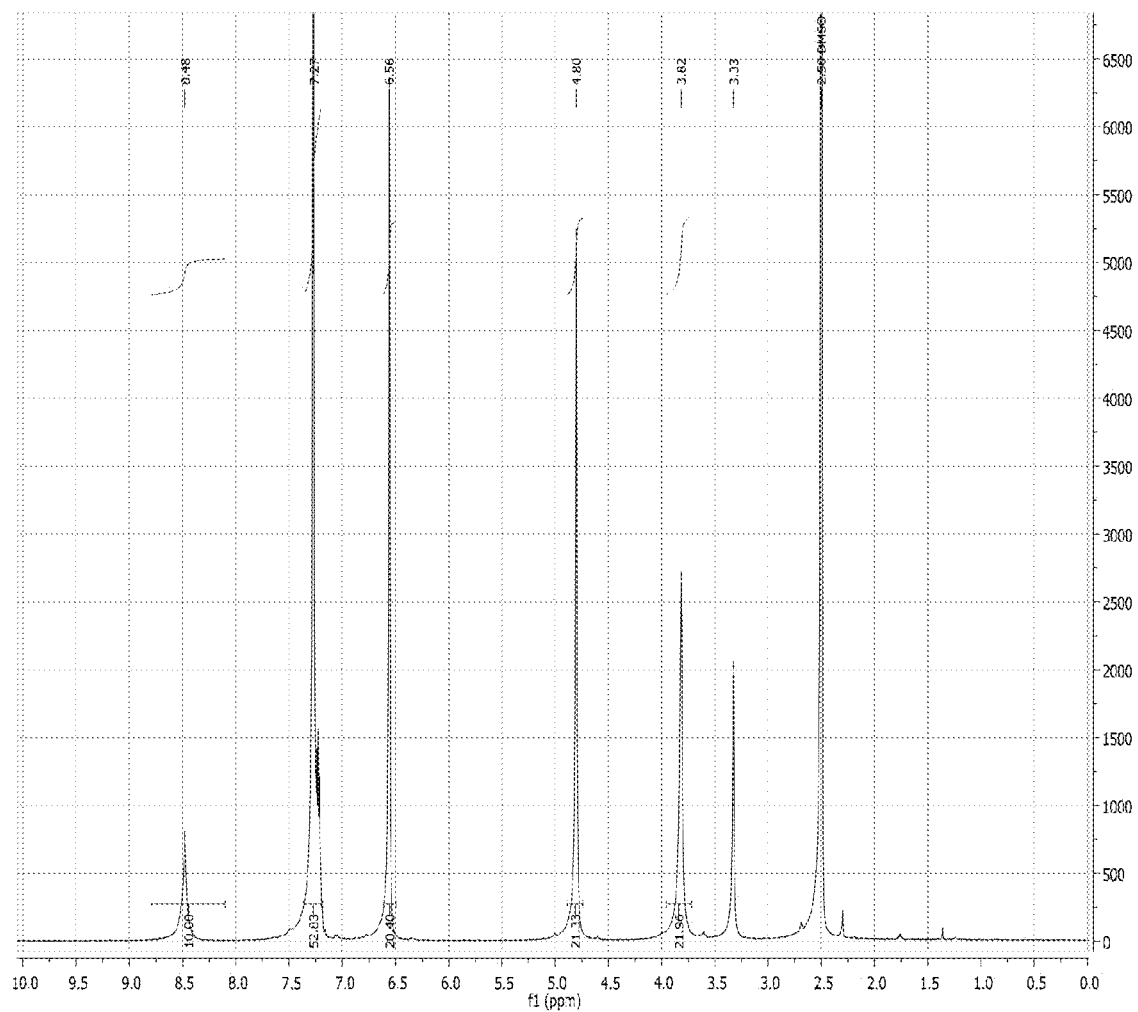
Figure 6.2 : Fraction P7 (Calix[10]arene)

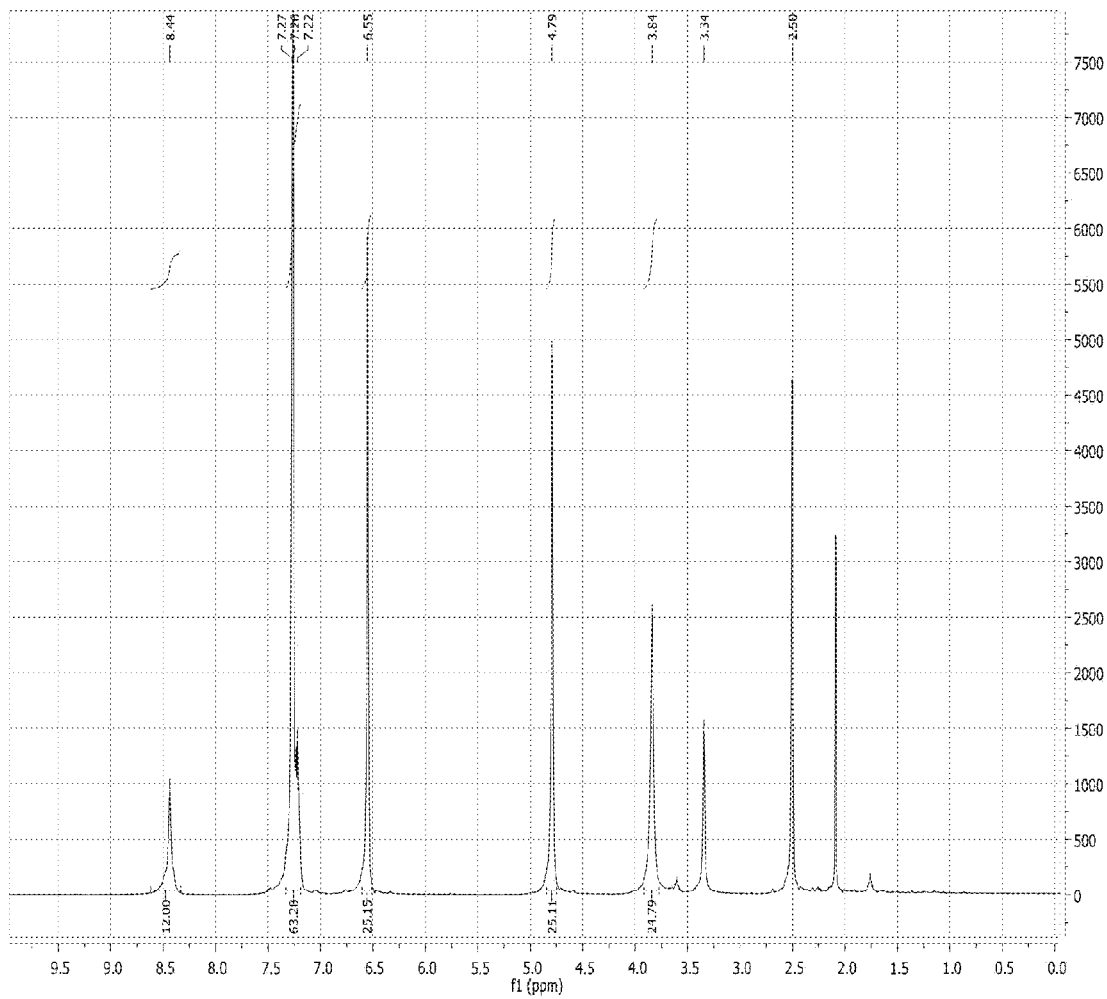
Figure 6.3 : Fraction P10 (Calix[12]arene)

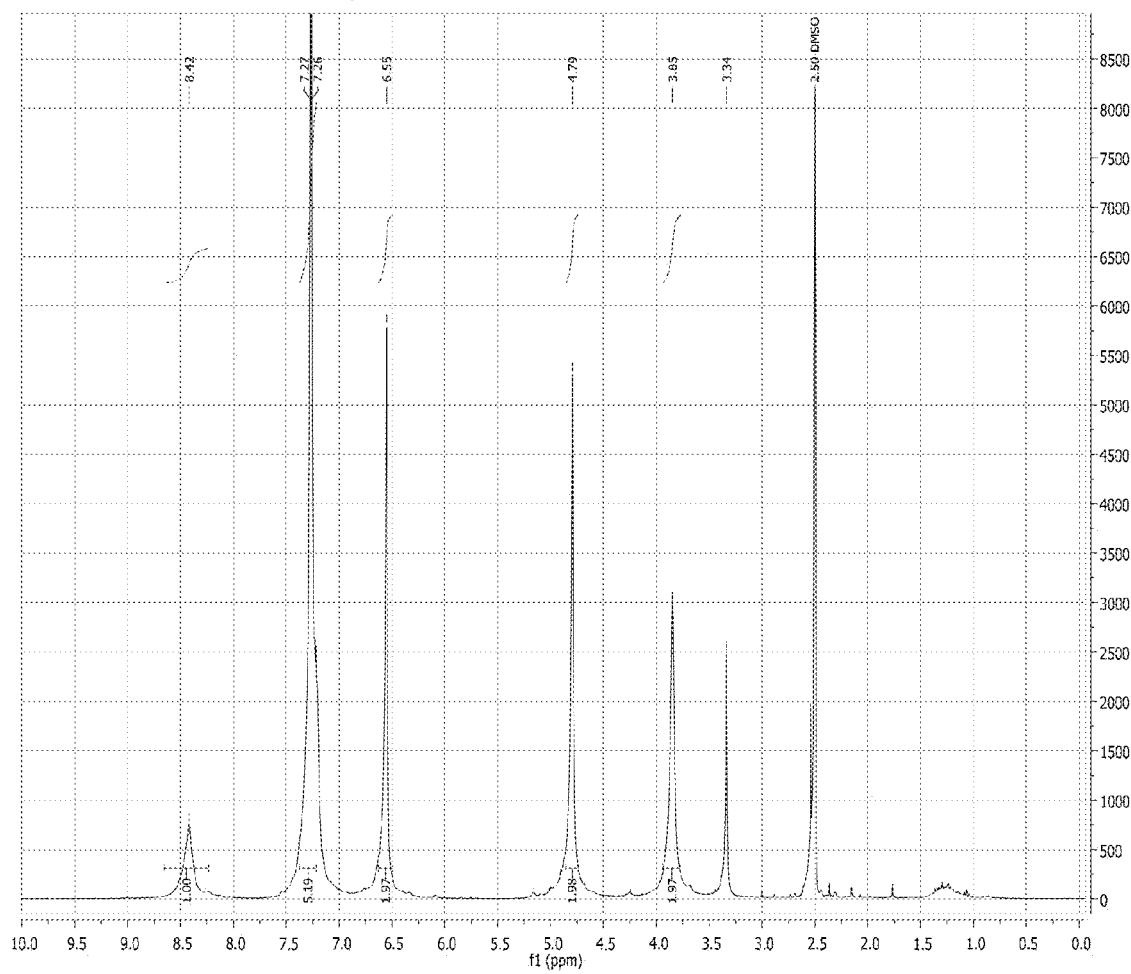
Figure 6.4 : Fraction F16 (calix[13]arene)

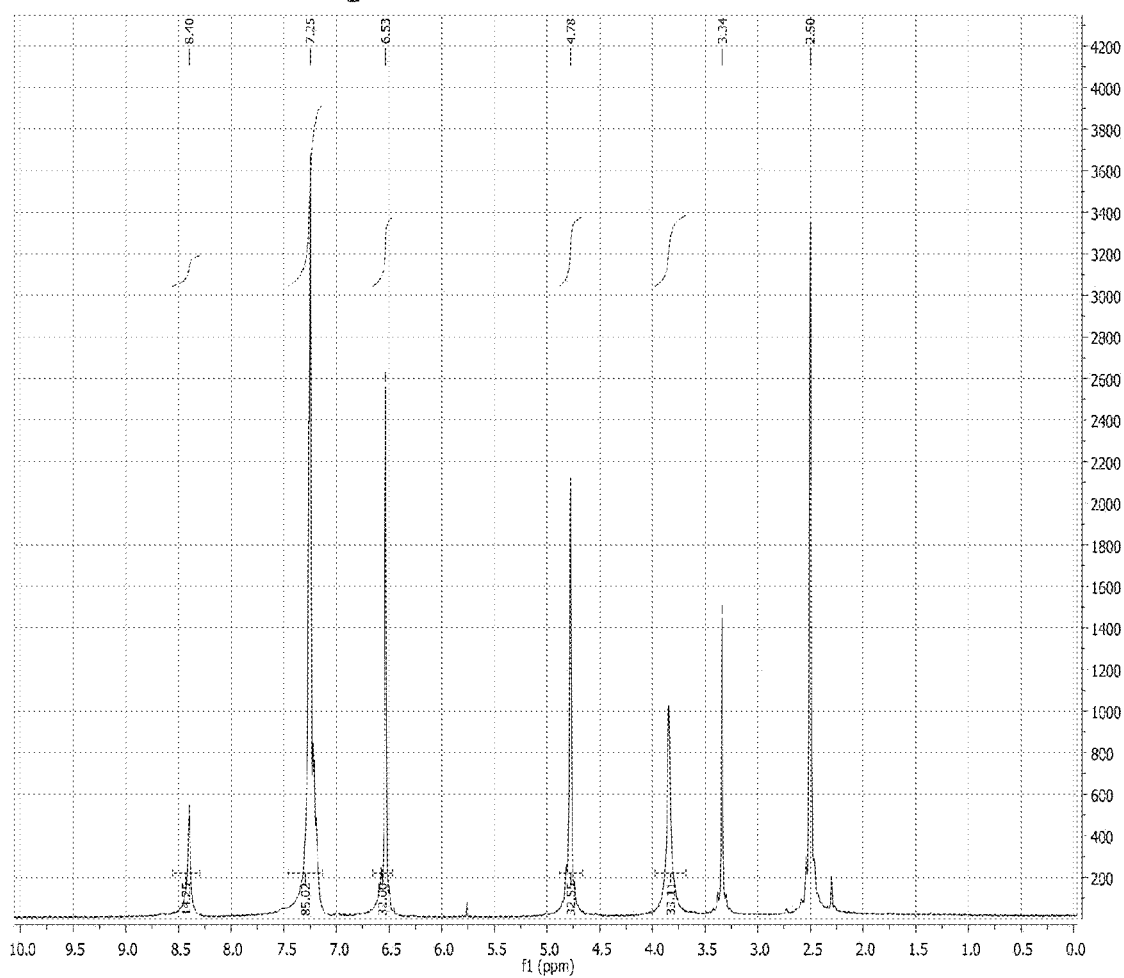
Figure 6.5 : Fraction P4 (calix[16]arene)

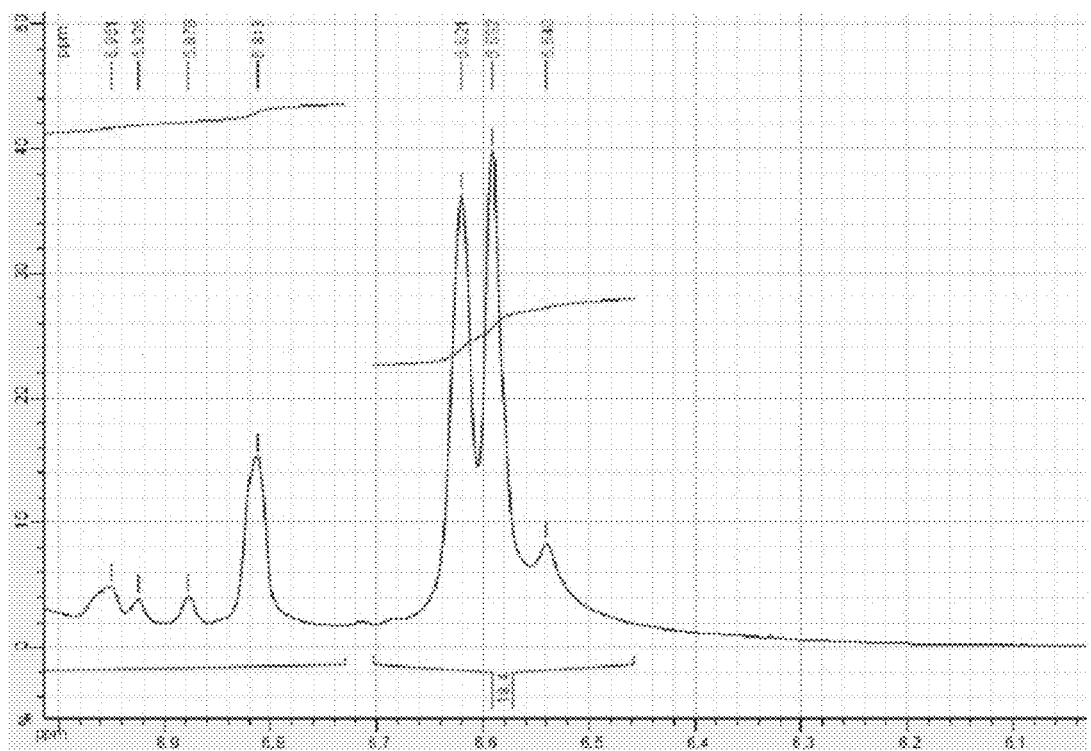
FIGURE 8.1

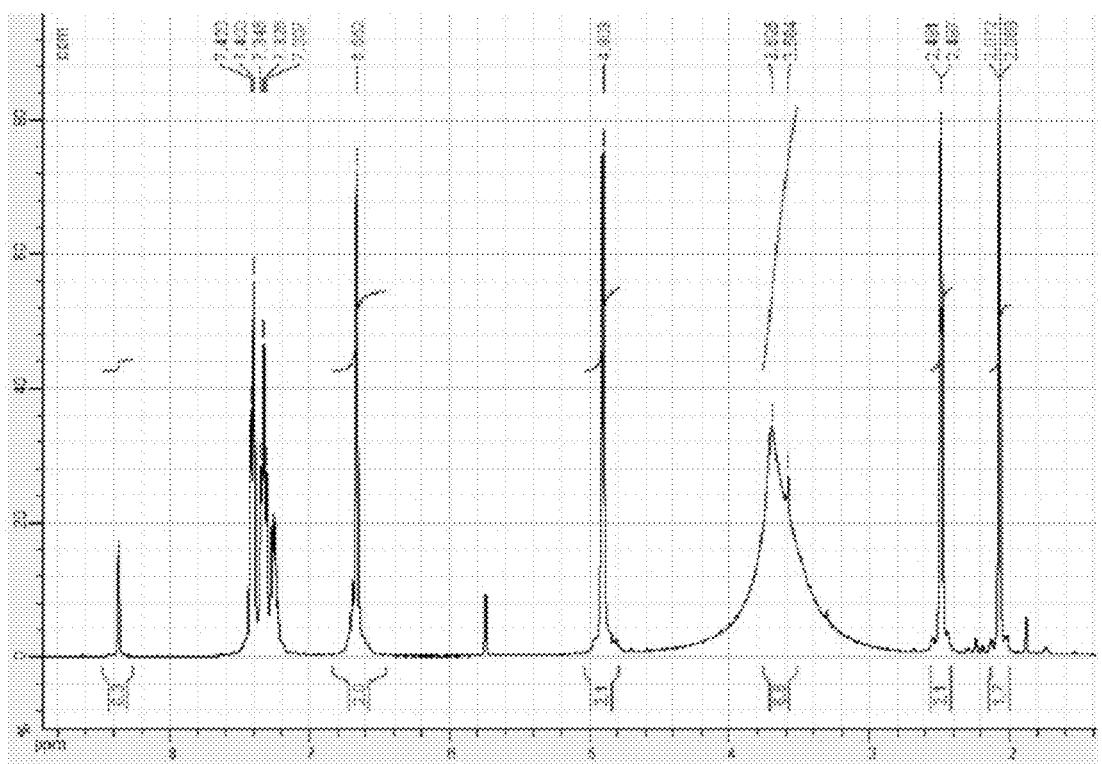
FIGURE 8.2

METHOD FOR THE HIGH-YIELD PRODUCTION OF P-(R-OXY)CALIX[9-20] ARENES

This application is a 371 of PCT/FR2013/051988, filed on Aug. 28, 2013.

The present invention relates to a process for the high-yield preparation of p-(R-oxy)calix[9-20]arenes.

The calixarenes have been the subject of particular study in the last ten years owing to the immense possibilities offered by these easily accessible macrocycles. These macrocycles are cup-shaped, the cavity generally being less than or equal to approximately 1 nm.

Some of the properties most studied include the phenomena of recognition of the inorganic ions and organic molecules, the supramolecular assemblies or also the synthesis of nanoparticles, among other things.

In most cases, these studies were carried out with calixarenes functionalized with a p-(t-butyl) or with calixarenes obtained by chemical modification of these p-(t-butyl)calixarenes, since the synthesis of p-(t-butyl)calixarenes is by far the most documented since the pioneering work of Gutsche et al.

D. Gutsche, *Calixarenes: An Introduction*, The Royal Society of Chemistry, Cambridge, 2008. Z. Asfari, V. Böhmer, J. Harrowfield, J. Vicens, *Calixarenes* 2001, Kluwer, Dordrecht, the Netherlands, 2001.

Consequently, the use of other monomers of the functionalized phenol type for the synthesis of calixarenes is largely unexplored, even if one-stage syntheses of other p-(alkyl) calixarenes are known (T. Patrick, P. Egan, *J. Org. Chem.* 1977, 42, 382; T. Patrick, P. Egan, *J. Org. Chem.* 1978, 43, 4280; Z. Asfari, J. Vicens, *Tetrahedron Lett.* 1988, 29, 2659; F. Vocanson, M. Perrin, R. Lamartine, *J. Inclusion Phenom. Macrocyclic Chem.* 2001, 39, 127; Jerry L. Atwood et al.; *Org. Lett.* 1999, 1, 1523).

The p-substituted calixarenes are usually obtained in a mixture of p-calix[4, 5, 6, 7, 8]arenes by reaction of a p-substituted phenol with paraformaldehyde in the presence of at least one base such as potassium hydroxide or sodium hydroxide (B. Dahwan et al., *Macromolec. Chem.* 1987, 188, 921; C. D. Gutsche et al., *Org. Synth.* 1990, 68, 234; C. D. Gutsche et al., *Org. Synth.* 1990, 68, 238).

In general, the p-(alkyl)calix[8]arenes are the calixarenes that are obtained most easily, as they correspond to the kinetic product of the polycondensation reaction. For their part, the p-(alkyl)calix[4]arenes correspond to the thermodynamic product.

In most cases, withdrawal or substitution of the hydroxyl function of these calixarenes from the alkyl position to para, when it is possible, is at best difficult. In the commonest case of the p-(t-butyl)calixarenes, it is generally a multi-stage process. Firstly, a reagent of the Lewis acid type is generally combined with a phenol to remove the t-butyl group, then secondly, another function may be introduced in place of the t-butyl group, having halogenated the position beforehand. As the reaction is not quantitative, "deterbutylation" becomes problematic, in particular when the number of calixarene units increases. The presence of by-products limits the yield, makes a purification stage necessary and restricts the purity of the product. This may limit the final yield of fully deprotected product, as well as the use thereof.

The p-(benzyloxy)calixarenes represent a very useful alternative to the p-(alkyl)calixarenes. The (benzyloxy)phenol units are in fact reduced quantitatively to phenols by hydrogenolysis catalysed by palladium on charcoal, allowing easy post-functionalization.

p-(Benzyloxy)calix[6]arene is a calixarene already described in the literature in the neutralized form but obtained either as a very minority product of the synthesis of p-(benzyloxy)calix[8]arene, after several stages of purification with a yield of 1 to 2% (A. Casnati et al., *J. Am. Chem. Soc* 2001, 123, 12182), or in the relatively impure form with a purity of the order of 80% (V. Huc et al., *Eur. J. Org. Chem* 2010, 6186).

p-(Benzyloxy)calix[7]arene comprises 7 repeat units in its structure. This size of ring is usually considered difficult to obtain in the field of calixarene chemistry. In fact, earlier studies show that calixarenes comprising an odd number of units are difficult to access. In the precise case of p-(benzyloxy)calix[7]arene, this product is already described as a very minority by-product of the synthesis of other calixarenes with yields of less than 10%, using complex purification procedures including column chromatography purifications (V. Huc et al., *Eur. J. Org. Chem.* 2010, 6186). Other calix[7] arenes are also known, in particular in the p-(t-butyl) series, but there too the yields are low (For the p-(t-butyls): A. Ninegawa et al. 1982, *Macromol. Chem. Rapid. Chem.*, 3, 65; Y. Nakamoto et al. *Macromol. Chem. Rapid. Chem.* 1982, 3, 705; F. Vocanson et al., *New. J. Chem.* 1995, 19, 825. For the p-(benzyls): J. L. Atwood et al. 1999, *Org. Lett.*, 1, 1523).

p-(Benzyloxy)calix[7]arene in the monosalified form is not described in the literature and obtaining it would open up the way to novel mono-functionalized calix[7]arenes, the phenol salt being much more nucleophilic than the adjacent neutral phenols.

p-(Benzyloxy)calix[8]arene is obtained in the prior art with a yield of 48% by reaction of the p-(benzyloxy)phenol in the presence of formaldehyde with a base selected from sodium hydroxide, potassium hydroxide or lithium hydroxide, the base being at a concentration of 0.02 equivalent with respect to the p-(benzyloxy)phenol (A Casnati and al, *J. Org. Chem.* 1997, 62, 6236).

Few documents describe the synthesis of large calixarenes, i.e. comprising from 9 to 20 repeat units.

Thus patent CA 2,251,070 describes the production of calixarenes comprising 9 and 11-14 repeat units with low yields, by a two-stage process by reaction of a p-(alkyl) or p-(aralkyl)phenol in an aqueous medium in the presence of a base in a quantity of less than 0.5 eq and then heating in an organic solvent without water.

This patent does not describe the production of p-(R-oxy) calix[9-20]arenes.

The article by Gutsche et al. (*J. Am. Chem. Soc.* 1999, 121, 4136) describes the production of p-(t-butyl)calix[9-20]arenes in an acid medium but not the production of p-(R-oxy) calixarenes.

Consequently, it remains an open question as to how to obtain calixarenes that can be easily functionalized on the high crown with a large variety of chemical groups under mild conditions and, in particular, how to obtain calixarenes such as the p-(R-oxy)calix[9-20]arenes with good yields.

One of the aims of the invention is the manufacture of p-(R-oxy)calix[9-20]arenes (also called large calixarenes) with cumulative yields greater than 5%, in particular greater than 10%, 20%, 30%, 40% or 50%, in particular greater than 50%.

Another aim of the invention is to provide a single-stage synthesis process making it possible to:

obtain a mixture of twelve p-(R-oxy)calix[9-20]arenes or of a few p-(R-oxy)calix[9-20]arenes, isolated and pure, or a mixture of two, three, four, five, six, seven, eight, nine, ten or eleven out of the twelve, as well as a single-stage procedure for the crystallization of the mixture of calixarenes, making it possible to obtain them pure, in particular free from the p-(benzyloxy)calix[5-8]arenes.

Another aim of the invention is to provide a p-(R-oxy)calix [7]arene in the form of the sodium or potassium monosalt.

Yet another aim is the use of p-(R-oxy)calix[9-20]arenes in a mixture or separately for the constitution of a material.

The present invention relates to the use of at least one base, in particular selected from potassium hydroxide, sodium hydroxide, lithium hydroxide, rubidium hydroxide or caesium hydroxide, with at least one phenol substituted in position 4 of following formula (I):

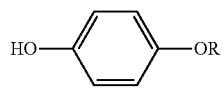
(I)

in which R is selected from:
a benzyl group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)ORaORb$, $R_a$ and $R_b$ representing independently of one another a linear or branched $C_1$-$C_{20}$ alkyl,
a linear or branched $C_1$-$C_{20}$ alkyl group,
a linear or branched PEG-1 to 10, the —OH end group of which is alkylated with a linear or branched $C_1$-$C_{20}$ alkyl,
a source of formaldehyde and an organic solvent,
the mixture of said base, said phenol, said source of formaldehyde and said organic solvent constituting a reaction medium,
said reaction medium being heated and said base being at a total concentration of more than 0.5 equivalent, in particular comprised from more than 0.5 equivalent to 1.5 equivalent, advantageously from more than 0.5 equivalent to 1.2 equivalent, in particular equal to 0.6 equivalent, with respect to the aforesaid phenol substituted in position 4 of formula (I), for carrying out a reaction for the preparation of a p-(R-oxy)calixarene selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or of a mixture of said p-(R-oxy)calixarenes.

The present invention also relates to the use of at least one base, in particular selected from potassium hydroxide, sodium hydroxide, lithium hydroxide, rubidium hydroxide or caesium hydroxide, with at least one phenol substituted in position 4 of following formula (I):

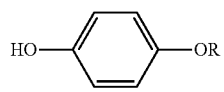
(I)

in which R is selected from:
a benzyl group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)ORaOR_b$, $R_a$ and $R_b$ representing independently of one another a linear or branched $C_1$-$C_{20}$ alkyl,
a linear or branched $C_1$-$C_{20}$ alkyl group,
a linear or branched PEG-1 to 10, the —OH end group of which is alkylated with a linear or branched $C_1$-$C_{20}$ alkyl,
a source of formaldehyde and an organic solvent,
the mixture of said base, said phenol, said source of formaldehyde and said organic solvent constituting a reaction medium,
said reaction medium being heated and said base being at a total concentration of more than 0.5 equivalent, in particular comprised from more than 0.5 equivalent to 1.5 equivalent, advantageously from more than 0.5 equivalent to 1.2 equivalent, in particular equal to 0.6 equivalent, with respect to the aforesaid phenol substituted in position 4 of formula (I), for carrying out a reaction for the preparation of a p-(R-oxy)calixarene selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or a mixture of at least two of said p-(R-oxy)calixarenes in which said at least two p-(R-oxy)calixarenes are present in said mixture each at a level of at least 5 mol. %.

The heating depends on the organic solvent used and is comprised from 50° C. to 250° C., in particular under reflux, i.e. at the boiling point of the organic solvent used.

The term base denotes any base of the metal hydroxide, tertiary amine, carbonate, sulphate, carboxylate, hydride, alcoholate or organolithium type, for example, or also an organic base of the amine type in combination with a metal salt (CsI for example, which is relatively soluble in the organic phase).

The term $C_1$-$C_{20}$ alkyl used throughout the description denotes a linear or branched alkyl group comprising 1 to 20 carbon atoms.

By linear $C_1$ to $C_{20}$ alkyl group, is meant: a methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl group, as well as all their isomers.

By branched alkyl group, is meant an alkyl group as defined above comprising substituents selected from the list of the linear alkyl groups defined above, said linear alkyl groups also being capable of being branched.

By $C_3$ to $C_{20}$ cycloalkyl group is meant a cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentadecyl, cyclohexadecyl, cycloheptadecyl, cyclooctadecyl, cyclononadecyl and cycloeicosyl group.

Such cycloalkyl groups may themselves be substituted with one or more linear or branched alkyl group(s) as defined above.

The expression "source of formaldehyde" means that paraformaldehyde, trioxane or formaldehyde in an aqueous solution such as formalin or formol can be used.

The term organic solvent denotes any polar, or preferably non-polar, solvent the boiling point of which is greater than approximately 50° C., in particular a solvent the boiling point of which is comprised from 50 to 250° C., in particular xylene, toluene, octane, diphenyl ether, mesitylene, chlorobenzene, dichlorobenzene, trichlorobenzene.

The expression "reaction medium" means the mixture of the different components, comprising the base or bases, the phenol or phenols substituted in position 4 of formula (I), the source of formaldehyde and the organic solvent.

When said mixture has just been constituted, it is called an initial reaction medium, i.e. a reaction medium in which the reaction for the preparation of the p-(R-oxy)calixarenes has not yet been carried out, in particular before any heating of said mixture of the different compounds.

When the reaction for the preparation of the p-(R-oxy)calix [9-20]arenes is carried out, in particular after heating of said mixture of the different compounds, the reaction medium is called the final reaction medium.

The p-(R-oxy)calix[9-20]arenes have the following structure:

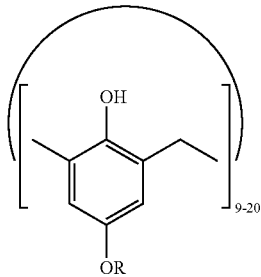

and are therefore constituted by:
a mixture of two, three, four, five, six, seven, eight, nine, ten, eleven or twelve p-(R-oxy)calixarenes selected from the group of p-(R-oxy)[9-20]calixarenes, irrespective of the proportion of each p-(R-oxy)calixarene present in the mixture and may also be referred to throughout the description as "large p-(R-oxy)calixarenes",
or one of the twelve p-(R-oxy)calixarenes, purified or pure, selected from the group of p-(R-oxy)calixarenes of 9 to 20.

In particular, the p-(R-oxy)calix[9-20]arenes have the following structure:

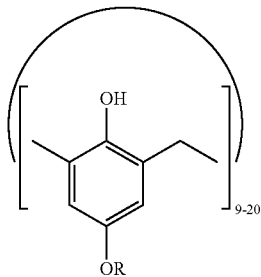

and are therefore constituted by:
a mixture of two, three, four, five, six, seven, eight, nine, ten, eleven or twelve p-(R-oxy)calixarenes selected from the group of p-(R-oxy)[9-20]calixarenes, irrespective of the proportion of each p-(R-oxy)calixarene present in the mixture, said p-(R-oxy)calixarenes being present in said mixture each at a level of at least 5 mol. %, and can also be referred to throughout the description as "large p-(R-oxy)calixarenes",
or one of the twelve p-(R-oxy)calixarenes, purified or pure, selected from the group of p-(R-oxy)calixarenes from 9 to 20.

Throughout the description, the term "purified" or "pure" denotes a compound having a purity greater than 90%.

The mixture of p-(R-oxy)calix[9-20]arenes or the purified p-(R-oxy)calixarenes are as a general rule obtained in the neutralized form after neutralization of the base present in the final reaction medium.

By the expression "in the neutralized form", is meant a purified p-(R-oxy)calixarene in which all the hydroxyls of the phenol groups have been neutralized, i.e. are in the non-salified OH form.

Without neutralization of the base, the mixture of p-(R-oxy)calix[9-20]arenes or the purified p-(R-oxy)calixarenes are obtained in the potentially salified form (according to the base concentration and the number of calixarene units), i.e. at least one of the free phenol groups is in the salified form with the metal cation originating from the base, in particular the mixture of p-(R-oxy)calixarenes or the purified p-(R-oxy) calixarenes are obtained in the mono-salified form, i.e. a single one of the free phenol groups is in the salified form with the metal cation originating from the base.

The inventors have surprisingly found that the combination of at least one base such as potassium hydroxide, sodium hydroxide, lithium hydroxide, rubidium hydroxide or caesium hydroxide with a p-(R-oxy)phenol and with a total base concentration greater than 0.5 equivalent, in particular comprised from more than 0.5 equivalent to 1.5 equivalent, advantageously from 0.5 equivalent to 1.2 equivalent, in particular equal to 0.6 equivalent, with respect to said p-(R-oxy)phenol, made it possible to obtain a mixture of twelve p-(benzyloxy) calix[9-20]arenes as a majority or purified, with good yields.

This result is all the more unexpected as the use of a base concentration less than or equal to 0.5 equivalent, such as potassium hydroxide, sodium hydroxide or caesium hydroxide with a p-(R-oxy)phenol such as p-(benzyloxy)phenol leads mainly to a mixture of p-(benzyloxy)calix[6-8]arenes with good yields.

In an advantageous embodiment, the base concentration is comprised from more than 0.5 equivalent to 1.2 equivalent, preferentially from more than 0.5 equivalent to 1.1 equivalent, preferentially from more than 0.5 equivalent to 1 equivalent, preferentially from more than 0.5 equivalent to 0.9 equivalent, preferentially from more than 0.5 equivalent to 0.8 equivalent, preferentially from more than 0.5 equivalent to 0.7 equivalent, preferentially from more than 0.5 equivalent to 0.6 equivalent, in particular 0.6 equivalent.

In another embodiment, the base concentration is comprised from 0.6 equivalent to 1.2 equivalent, preferentially from 0.6 equivalent to 1.1 equivalent, preferentially from 0.6 equivalent to 1 equivalent, preferentially from 0.6 equivalent to 0.9 equivalent, preferentially from 0.6 equivalent to 0.8 equivalent, preferentially from 0.6 equivalent to 0.7 equivalent, in particular 0.6 equivalent.

With the exception of rubidium hydroxide, a concentration less than or equal to 0.5 equivalent, the p-(benzyloxy)calixarenes obtained correspond mainly to the p-(benzyloxy)calix [6-8]arenes.

In an advantageous embodiment, the present invention relates to the use of at least one base, in particular selected from potassium hydroxide, sodium hydroxide, lithium hydroxide, rubidium hydroxide or caesium hydroxide, with at least one phenol substituted in position 4 of formula (I) as defined above, in which the phenol substituted in position 4 of formula (I) is selected from 4-benzyloxyphenol or 4-octyloxyphenol.

In an advantageous embodiment, the present invention relates to the use of at least one base, in particular selected from potassium hydroxide, sodium hydroxide, lithium hydroxide, rubidium hydroxide or caesium hydroxide, with at least one phenol substituted in position 4 of formula (I) as defined above, in which the phenol substituted in position 4 of formula (I) is selected from 4-benzyloxyphenol, 4-octyloxyphenol or 4-methoxyphenol.

In an advantageous embodiment, the present invention relates to the use of at least one base, in particular selected from potassium hydroxide, sodium hydroxide, lithium hydroxide, rubidium hydroxide or caesium hydroxide, with at least one phenol substituted in position 4 of formula (I), in particular selected from 4-benzyloxyphenol or 4-octyloxyphenol, as defined above, in which the initial reaction medium before the start of the reaction is substantially devoid of water.

In an advantageous embodiment, the present invention relates to the use of at least one base, in particular selected from potassium hydroxide, sodium hydroxide, lithium hydroxide, rubidium hydroxide or caesium hydroxide, with at least one phenol substituted in position 4 of formula (I), in particular selected from 4-benzyloxyphenol, 4-octyloxyphenol or 4-methoxyphenol, as defined above, in which the initial reaction medium before the start of the reaction is substantially devoid of water.

The expression "substantially devoid of water" signifies that the proportion of water present in the initial reaction medium is less than or equal to 5% by weight in the reaction medium, or at trace levels.

The water present in the initial reaction medium originates only from the base introduced, optionally in an aqueous solution, such as, for example, rubidium hydroxide, caesium hydroxide, sodium hydroxide or potassium hydroxide, and from the residual quantity present in the solvent and the reagents constituting the reaction medium such as xylene, the substituted phenol or the source of formaldehyde.

The water present in the final reaction medium after completion of the reaction originates only from the reaction itself and from the base used, with no addition of external water being carried out before the completion of the reaction.

In an advantageous embodiment, the present invention relates to the use of at least one base, with at least one phenol substituted in position 4 of formula (I), in particular selected from 4-benzyloxyphenol or 4-octyloxyphenol, the initial reaction medium before the start of the reaction being in particular substantially devoid of water, as defined above, in which the source of formaldehyde is para-formaldehyde and the organic solvent is xylene.

In an advantageous embodiment, the present invention relates to the use of at least one base, with at least one phenol substituted in position 4 of formula (I), in particular selected from 4-benzyloxyphenol, 4-octyloxyphenol or 4-methoxyphenol, the initial reaction medium before the start of the reaction being in particular substantially devoid of water, as defined above, in which the source of formaldehyde is para-formaldehyde and the organic solvent is xylene.

In these embodiments, the formaldehyde and the base used are non-aqueous. The water present in the initial reaction medium originates only from the residual quantity present in the reagents constituting the reaction medium such as the base, the solvent or the source of formaldehyde.

The water present in the final reaction medium after completion of the reaction originates only from the reaction itself, as the reaction for the preparation of the p-(R-oxy)calix[9-20]arenes leads to the formation of water, with no addition of external water being carried out before the completion of the reaction.

Advantageously, the base used is non-aqueous and corresponds to tBuOK or tBuONa.

In an advantageous embodiment, the present invention relates to the use of at least one base, in particular selected from potassium hydroxide, sodium hydroxide, lithium hydroxide, rubidium hydroxide or caesium hydroxide, with at least one phenol substituted in position 4 of formula (I), in particular selected from 4-benzyloxyphenol or 4-octyloxyphenol, the initial reaction medium before the start of the reaction being in particular substantially devoid of water, the source of formaldehyde being in particular para-formaldehyde and the organic solvent xylene, as defined above, in which said base is selected from caesium hydroxide or rubidium hydroxide, in particular in an aqueous solution.

In an advantageous embodiment, the base used is caesium hydroxide or rubidium hydroxide, the phenol substituted in position 4 is 4-benzyloxyphenol, and the mixture of p-(benzyloxy)calix[9-20]arenes obtained is constituted mainly by p-(benzyloxy)calix[9]arene, p-(benzyloxy)calix[10]arene, p-(benzyloxy)calix[12]arene, p-(benzyloxy)calix[13]arene, p-(benzyloxy)calix[16]arene in which the p-(benzyloxy)calix[12]arene is itself the majority constituent and also comprises p-(benzyloxy)calix[5]arene in a proportion of approximately 10 mol. % (determined by NMR).

In an advantageous embodiment, the present invention relates to the use of at least one base, in particular selected from potassium hydroxide, sodium hydroxide, lithium hydroxide, rubidium hydroxide or caesium hydroxide, with at least one phenol substituted in position 4 of formula (I), in particular selected from 4-benzyloxyphenol or 4-octyloxyphenol, the initial reaction medium before the start of the reaction being in particular substantially devoid of water, the source of formaldehyde being in particular para-formaldehyde and the organic solvent xylene, as defined above, in which said base is selected from sodium hydroxide or potassium hydroxide, in particular in an aqueous solution.

In an advantageous embodiment, the present invention relates to the use of at least one base, in particular selected from potassium hydroxide, sodium hydroxide, lithium hydroxide, rubidium hydroxide or caesium hydroxide, with at least one phenol substituted in position 4 of formula (I), in particular selected from 4-benzyloxyphenol or 4-octyloxyphenol, the initial reaction medium before the start of the reaction being in particular substantially devoid of water, the source of formaldehyde being in particular para-formaldehyde and the organic solvent xylene, said base being selected from sodium hydroxide or potassium hydroxide as defined above, in which said mixture of said p-(R-oxy)calix[9-20]arenes also comprises a p-(R-oxy)calix[7]arene in the form of the sodium or potassium monosalt, and/or a p-(R-oxy)calix[6]arene depending on the base used.

In this embodiment, the reaction leads mainly to a mixture of p-(R-oxy)calix[9-20]arenes (between 5 and 10 mol. %) and mainly to a p-(R-oxy)calix[7]arene in the form of the sodium or potassium monosalt (between 50 and 95 mol. %) which can be isolated before neutralization of the base, and an isolated p-(R-oxy)calix[6]arene in a small proportion in the acid form after neutralization.

In a more advantageous embodiment, the phenol used is 4-benzyloxyphenol or 4-octyloxyphenol.

The Inventors have found that when at least one base, selected from potassium hydroxide and sodium hydroxide, said base being at a total concentration of more than 0.5 equivalent, in particular comprised from more than 0.5 equivalent to 1.5 equivalent, advantageously from more than 0.5 equivalent to 1.2 equivalent, in particular equal to 0.6 equivalent, with respect to the aforesaid phenol substituted in position 4 of formula (I), is reacted with:

at least one phenol substituted in position 4 of formula (I) as defined above, in particular 4-benzyloxyphenol or 4-octyloxyphenol,
a source of formaldehyde and an organic solvent constituting a reaction medium, the initial reaction medium being substantially devoid of water,
oligomers are formed beforehand in order to then produce a phenolic dimer substituted in position 4 of following formula (II):

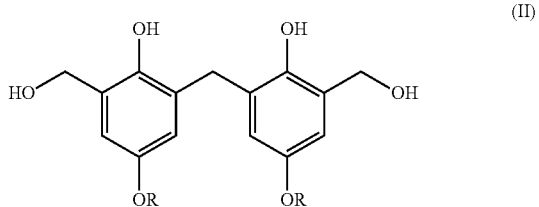

in which R is as defined in formula (I) above.

When said dimer is left to react, it then leads to a mixture of p-(R-oxy)calix[9-20]arenes obtained as a minority, of p-(R-oxy)calix[7]arene in the form of the sodium or potassium monosalt, of p-(R-oxy)calix[6]arene and of p-(R-oxy)calix[8]arene, these last three compounds being obtained as a majority.

According to another aspect, the present invention relates to a process for the preparation of:
a p-(R-oxy)calixarene selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or
a mixture of said p-(R-oxy)calix[9-20]arenes,
comprising a stage of bringing a base, in particular selected from potassium hydroxide, sodium hydroxide, lithium hydroxide, rubidium hydroxide or caesium hydroxide, into contact with at least one phenol substituted in position 4 of following formula (I):

in which R is selected from:
a benzyl group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing independently of one another a linear or branched $C_1$-$C_{20}$ alkyl,
a linear or branched $C_1$-$C_{20}$ alkyl group,
a linear or branched PEG-1 to 10, the —OH end group of which is alkylated with a linear or branched $C_1$-$C_{20}$ alkyl,
a source of formaldehyde and an organic solvent,
said reaction medium being heated and the mixture of said base, said phenol, said source of formaldehyde and said organic solvent constituting a reaction medium,
said base being at a total concentration comprised from more than 0.5 equivalent to 1.5 equivalent, advantageously from more than 0.5 equivalent to 1.2 equivalent, in particular equal to 0.6 equivalent with respect to said at least one phenol substituted in position 4 of formula (I).

The heating depends on the organic solvent used and is comprised from 50° C. to 250° C., in particular under reflux, i.e. at the boiling point of the organic solvent used.

The term base denotes any base of the metal hydroxide, metal alcoholate such as tBuOK or tBuONa, tertiary amine, carbonate, sulphate, carboxylate, hydride or organolithium type, for example or the use of an amine-type organic base in combination with a metal salt (CsI for example, which is relatively soluble in an organic phase).

The expression "source of formaldehyde" signifies that paraformaldehyde, trioxane or formaldehyde in an aqueous solution such as formalin or formol can be used.

The term organic solvent denotes any non-polar solvent the boiling point of which is greater than approximately 50° C., in particular a solvent the boiling point of which is comprised from 50 to 250° C., in particular xylene, toluene, octane, diphenyl ether, mesitylene, chlorobenzene, dichlorobenzene, trichlorobenzene.

In this embodiment, the initial reaction medium, i.e. after introduction of all the reagents into the solvent before heating, can also contain added water in a proportion of 1 to 10% by weight.

The present invention also relates to a process for the preparation of:
a p-(R-oxy)calixarene selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or
a mixture of at least two of said p-(R-oxy)calix[9-20]arenes in which said at least two p-(R-oxy)calixarenes are present in said mixture each at a level of at least 5 mol. %,
comprising a stage of bringing a base, in particular selected from potassium hydroxide, sodium hydroxide, lithium hydroxide, rubidium hydroxide or caesium hydroxide, into contact with at least one phenol substituted in position 4 of following formula (I):

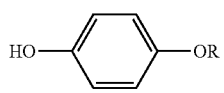

in which R is selected from:
a benzyl group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing independently of one another a linear or branched $C_1$-$C_{20}$ alkyl,
a linear or branched $C_1$-$C_{20}$ alkyl group,
a linear or branched PEG-1 to 10, the —OH end group of which is alkylated with a linear or branched $C_1$-$C_{20}$ alkyl, a source of formaldehyde and an organic solvent,
said reaction medium being heated and the mixture of said base, said phenol, said source of formaldehyde and said organic solvent constituting a reaction medium,
said base being at a total concentration comprised from more than 0.5 equivalent to 1.5 equivalent, advantageously from more than 0.5 equivalent to 1.2 equivalent, in particular equal to 0.6 equivalent with respect to said at least one phenol substituted in position 4 of formula (I).

In an advantageous embodiment, the base concentration is comprised from more than 0.5 equivalent to 1.2 equivalent by phenol, from more than 0.5 equivalent to 1.1 equivalent by phenol, from more than 0.5 equivalent to 1 equivalent by phenol, from more than 0.5 equivalent to 0.9 equivalent by phenol, preferentially from more than 0.5 equivalent to 0.8 equivalent, preferentially from more than 0.5 equivalent to 0.7 equivalent, preferentially from more than 0.5 equivalent to 0.6 equivalent, in particular 0.6 equivalent.

In another embodiment, the base concentration is comprised from 0.6 equivalent to 1 equivalent, preferentially from 0.6 equivalent to 0.9 equivalent, preferentially from 0.6 equivalent to 0.8 equivalent, preferentially 0.6 equivalent to 0.7 equivalent, in particular 0.6 equivalent.

In an advantageous embodiment, the present invention relates to a process for the preparation of:
a p-(R-oxy)calixarene selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or
a mixture of said p-(R-oxy)calix[9-20]arenes,
as defined above, in which said phenol substituted in position 4 of formula (I) is selected from 4-benzyloxyphenol or 4-octyloxyphenol.

In an advantageous embodiment, the present invention relates to a process for the preparation of:
a p-(R-oxy)calixarene selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or
a mixture of at least two of said p-(R-oxy)calix[9-20]arenes in which said at least two p-(R-oxy)calixarenes are present in said mixture each at a level of at least 5 mol. %,
as defined above, in which said phenol substituted in position 4 of formula (I) is selected from 4-benzyloxyphenol or 4-octyloxyphenol.

In an advantageous embodiment, the present invention relates to a process for the preparation of:
a p-(R-oxy)calixarene selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or
a mixture of said p-(R-oxy)calix[9-20]arenes,
in which said phenol substituted in position 4 of formula (I) is in particular selected from 4-benzyloxyphenol or 4-octyloxyphenol, as defined above,
in which the initial reaction medium before the start of the reaction is substantially devoid of water.

In an advantageous embodiment, the present invention relates to a process for the preparation of:
a p-(R-oxy)calixarene selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or
a mixture of at least two of said p-(R-oxy)calix[9-20]arenes in which said at least two p-(R-oxy)calixarenes are present in said mixture each at a level of at least 5 mol. %,
in which said phenol substituted in position 4 of formula (I) is in particular selected from 4-benzyloxyphenol or 4-octyloxyphenol, as defined above,
in which the initial reaction medium before the start of the reaction is substantially devoid of water.

The expression "substantially devoid of water" signifies that the proportion of water present in the initial reaction medium is less than 4.5% by weight in the reaction medium, or at trace levels.

The water present in the initial reaction medium originates only from the base introduced, optionally in an aqueous solution, such as, for example, rubidium hydroxide, caesium hydroxide, sodium hydroxide or potassium hydroxide, and from the residual quantity present in the solvent and the reagent constituting the reaction medium such as xylene, the substituted phenol or the source of formaldehyde.

In this embodiment, the formaldehyde is non-aqueous. The water present in the initial reaction medium originates only from the base used in an aqueous solution and from the residual quantity present in the solvent and the reagent constituting the reaction medium such as xylene, the substituted phenol or the source of formaldehyde.

In an advantageous embodiment, the present invention relates to a process for the preparation of:
a p-(R-oxy)calixarene selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or
a mixture of said p-(R-oxy)calix[9-20]arenes,
in which said phenol substituted in position 4 of formula (I) is in particular selected from 4-benzyloxyphenol or 4-octyloxyphenol, the initial reaction medium before the start of the reaction being in particular substantially devoid of water, as defined above, in which the source of formaldehyde is paraformaldehyde and the organic solvent is xylene.

In an advantageous embodiment, the present invention relates to a process for the preparation of:
a p-(R-oxy)calixarene selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or
a mixture of at least two of said p-(R-oxy)calix[9-20]arenes in which said at least two p-(R-oxy)calixarenes are present in said mixture each at a level of at least 5 mol. %,
in which said phenol substituted in position 4 of formula (I) is in particular selected from 4-benzyloxyphenol or 4-octyloxyphenol, the initial reaction medium before the start of the reaction being in particular substantially devoid of water, as defined above, in which the source of formaldehyde is paraformaldehyde and the organic solvent is xylene.

In an advantageous embodiment, the present invention relates to a process for the preparation of:
- a p-(R-oxy)calixarene selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or
- a mixture of said p-(R-oxy)calix[9-20]arenes, in which said phenol substituted in position 4 of formula (I) is in particular selected from 4-benzyloxyphenol or 4-octyloxyphenol, the initial reaction medium before the start of the reaction being in particular substantially devoid of water, the source of formaldehyde being in particular para-formaldehyde and the organic solvent being in particular xylene, as defined above, in which water is formed in the reaction medium during said preparation of said compound, said water being optionally substantially removed from the reaction medium during the reaction.

In this embodiment, the water is or is not removed from the reaction medium:

1) The water formed can be substantially removed during the reaction as it is formed by methods well known to a person skilled in the art such as a Dean-Stark device or flushing the reaction medium with a neutral gas, in particular nitrogen or argon.

In this case, the proportion of water present after completion of the reaction is less than 1% by weight.

2) The water formed can be stored during the reaction. The water present in the final reaction medium after completion of the reaction originates only from the reaction itself, the reaction mechanism of which leads to the formation of water and no addition of external water is carried out before completion of the reaction.

In an advantageous embodiment, the present invention relates to a process for the preparation of:
- a p-(R-oxy)calixarene selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or
- a mixture of at least two of said p-(R-oxy)calix[9-20]arenes in which said at least two p-(R-oxy)calixarenes are present in said mixture each at a level of at least 5 mol. %, in which said phenol substituted in position 4 of formula (I) is in particular selected from 4-benzyloxyphenol or 4-octyloxyphenol, the initial reaction medium before the start of the reaction being in particular substantially devoid of water, the source of formaldehyde being in particular para-formaldehyde and the organic solvent being in particular xylene, as defined above, in which water is formed in the reaction medium during said preparation of said compound, said water being optionally substantially removed from the reaction medium during the reaction.

In an advantageous embodiment, the present invention relates to a process for the preparation of:
- a p-(R-oxy)calixarene selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or
- a mixture of said p-(R-oxy)calix[9-20]arenes, in which said phenol substituted in position 4 of formula (I) is in particular selected from 4-benzyloxyphenol or 4-octyloxyphenol, the initial reaction medium before the start of the reaction being in particular substantially devoid of water, the source of formaldehyde being in particular para-formaldehyde and the organic solvent being in particular xylene, the water formed in the reaction medium during said preparation of said compound being optionally substantially removed from said reaction medium, as defined above, in which said base is selected from caesium hydroxide and rubidium hydroxide, in particular in an aqueous solution.

In this embodiment rubidium or caesium hydroxide are used in an initial reaction medium substantially devoid of water, or not, and the water formed during the reaction is substantially removed or retained in the reaction medium.

In an advantageous embodiment, the present invention relates to a process for the preparation of:
- a p-(R-oxy)calixarene selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or
- a mixture of at least two of said p-(R-oxy)calix[9-20]arenes in which said at least two p-(R-oxy)calixarenes are present in said mixture each at a level of at least 5 mol. %, in which said phenol substituted in position 4 of formula (I) is in particular selected from 4-benzyloxyphenol or 4-octyloxyphenol, the initial reaction medium before the start of the reaction being in particular substantially devoid of water, the source of formaldehyde being in particular para-formaldehyde and the organic solvent being in particular xylene, the water formed in the reaction medium during said preparation of said compound being optionally substantially removed from said reaction medium, as defined above, in which said base is selected from caesium hydroxide and rubidium hydroxide, in particular in an aqueous solution.

In an advantageous embodiment, the present invention relates to one of the processes for the preparation of:
- a p-(R-oxy)calixarene selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or
- a mixture of said p-(R-oxy)calix[9-20]arenes, as defined above, comprising the following stages:
a. bringing caesium and/or rubidium hydroxide, in particular in an aqueous solution, into contact with at least one phenol substituted in position 4 of formula (I), said base being at a total concentration comprised from more than 0.5 equivalent to 1.5 equivalent, advantageously from more than 0.5 equivalent to 1.2 equivalent, in particular equal to 0.6 equivalent with respect to said at least one phenol substituted in position 4 of formula (I), a source of formaldehyde, in particular of paraformaldehyde in an organic solvent then heating while optionally removing said water formed from the reaction medium,
in order to obtain:

a p-(R-oxy)calixarene selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or, a mixture of said p-(R-oxy)calix[9-20]arenes, in the salified form in the final reaction medium, b. neutralization of said salified form of said p-(R-oxy)calixarene or of said mixture in order to obtain said p-(R-oxy)calixarene or said mixture in the neutralized form.

In an advantageous embodiment, the present invention relates to one of the processes for the preparation of:

a p-(R-oxy)calixarene selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or a mixture of said p-(R-oxy)calix[9-20]arenes, as defined above, comprising the following stages:

a. bringing caesium and/or rubidium hydroxide, in particular in an aqueous solution, into contact with at least one phenol substituted in position 4 of formula (I), said base being at a total concentration comprised from more than 0.5 equivalent to 1.5 equivalent, advantageously from more than 0.5 equivalent to 1.2 equivalent, in particular equal to 0.6 equivalent with respect to said at least one phenol substituted in position 4 of formula (I), a source of formaldehyde, in particular of paraformaldehyde in an organic solvent then heating while optionally removing said water formed from the reaction medium, in order to obtain:

a p-(R-oxy)calixarene selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or, a mixture of at least two of said p-(R-oxy)calix[9-20]arenes in which said at least two p-(R-oxy)calixarenes are present in said mixture each at a level of at least 5 mol. %, in the salified form in the final reaction medium, b. neutralization of said salified form of said p-(R-oxy)calixarene or of said mixture in order to obtain said p-(R-oxy)calixarene or said mixture in the neutralized form.

In stage a., the rubidium and/or caesium hydroxide used can be in an aqueous solution or solid. When rubidium and/or caesium hydroxide is in an aqueous solution, the concentration of the base in an aqueous solution used is advantageously approximately 50% by weight. The source of formaldehyde can be aqueous or non-aqueous, in particular in the non-aqueous form and in particular it corresponds to paraformaldehyde.

The initial reaction medium can therefore be substantially devoid of water or not.

The organic solvent denotes any non-polar solvent the boiling point of which is greater than approximately 50° C., in particular a solvent the boiling point of which is comprised from 50 to 250° C., in particular xylene, toluene, octane, diphenyl ether, mesitylene, chlorobenzene, dichlorobenzene, trichlorobenzene, in particular the organic solvent is xylene.

The heating is comprised from 50° C. to 250° C., in particular it is carried out at the boiling point of the organic solvent used, for a period of time comprised from 30 minutes to 24 h in order to obtain said p-(R-oxy)calix[n]arene in which n is comprised from 9 to 20 or said mixture in the salified form in the final reaction medium.

In particular, the heating is comprised from 50° C. to 250° C., in particular it is carried out at the boiling point of the organic solvent used, for a period of time comprised from 4 to 24 h in order to obtain said p-(R-oxy)calix[n]arene in which n is comprised from 9 to 20 or said mixture in the salified form in the final reaction medium.

Advantageously, the heating is comprised from 50° C. to 250° C., in particular it is carried out at the boiling point of the organic solvent used, for a period of time comprised from 30 minutes to 4 h, in particular from 45 minutes to 2 h, more particularly for approximately 1 h, in order to obtain said p-(R-oxy)calix[n]arene in which n is comprised from 9 to 20 or said mixture in the salified form in the final reaction medium, the base used being in particular caesium hydroxide.

The water formed in the reaction medium during the reaction can be removed by techniques well known to a person skilled in the art, for example by means of a Dean-Stark device or flushing the reaction medium with a neutral gas, in particular nitrogen or argon.

In stage b., the neutralization is carried out with an acid, in particular in an aqueous solution, in particular HCl or $H_2SO_4$. Preferably HCl, which can be easily evaporated off.

Advantageously, the formaldehyde used is paraformaldehyde, the caesium and/or rubidium hydroxide are in an aqueous solution, the solvent used is xylene and the reaction time is comprised from 5 to 9 h, in particular 7 h.

Very advantageously, the formaldehyde used is paraformaldehyde, the caesium and/or rubidium hydroxide are in an aqueous solution, the solvent used is xylene and the reaction time is comprised from 30 minutes to 4 h, in particular from 45 minutes to 2 h, the reaction time being more particularly approximately 1 h.

In an advantageous embodiment, the reaction time of stage a. defined above is comprised from 30 min to 1 h in order to obtain firstly linear oligomers of phenolic units then, secondly, the dimer of formula (II) defined above, in the salified form, virtually quantitatively, which after said neutralization of said stage b., is obtained in the neutralized form.

When the heating is continued with the salified dimer, calixarenes of the invention are then formed.

In another advantageous embodiment, the reaction time for obtaining said p-(R-oxy)calixarene or a mixture of said p-(R-oxy)calix[9-20]arenes, in the salified form in the final reaction medium, is comprised from 30 minutes to 4 h, in particular from 45 minutes to 2 h, the reaction time being more particularly approximately 1 h, the base used being in particular caesium hydroxide.

Said mixture of p-(R-oxy)calixarene is at least 50% constituted by p-(R-oxy)calix[9-20]arenes, in particular 50% of a mixture comprising p-(R-oxy)calix[9]arene, p-(R-oxy)calix[10]arene, p-(R-oxy)calix[12]arene, p-(R-oxy)calix[13]arene, p-(R-oxy)calix[16]arene, as well as p-(R-oxy)calix[5]arene, in particular in a proportion of approximately 10 mol. %.

In an advantageous embodiment, the process defined above comprises an additional stage of purification of said p-(R-oxy)calixarene or of said mixture in the neutralized form, in particular by crystallization from a mixture of solvents based on DMSO in order to obtain in the solid said p-(R-oxy)calixarene or said mixture in the purified neutralized form, optionally followed by chromatography.

The additional stage of purification is carried out after stage b. defined above.

The solvent mixture based on an aprotic polar solvent, in particular based on DMSO or DMF, and in particular a DMSO/toluene or DMSO/acetone mixture, the DMSO being in a proportion of 5% to 50% by volume in the mixture of solvent, in particular 10%.

The second solvent can also be a toluene/acetone solvent mixture irrespective of the proportion of each of the two solvents, i.e.: acetone from 0.1 to 99.9% by weight and toluene: from 99.9 to 0.1% by weight.

In an advantageous embodiment, the mixture at least 50% constituted by p-(R-oxy)calix[9-20]arene and of p-(R-oxy)calix[5]arene, purified or non-purified, is a mixture at least 50% constituted by p-(benzyloxy)calix[9-20]arene and of p-(benzyloxy)calix[5]arene or at least 50% constituted by p-(octyloxy)calix[9-20]arene and of p-(octyloxy)calix[5]arene.

In an advantageous embodiment, the present invention relates to a process for the preparation of:
a p-(R-oxy)calixarene selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or
a mixture of said p-(R-oxy)calix[9-20]arenes,
in which said phenol substituted in position 4 of formula (I) is in particular selected from 4-benzyloxyphenol or 4-octyloxyphenol, the initial reaction medium before the start of the reaction being in particular substantially devoid of water, the source of formaldehyde being in particular para-formaldehyde and the organic solvent being in particular xylene, the water formed in the reaction medium during said preparation of said compound being optionally substantially removed from said reaction medium, as defined above, in which said base is selected from sodium hydroxide or potassium hydroxide, in particular in an aqueous solution.

In this embodiment, potassium hydroxide or sodium hydroxide are used in an initial reaction medium substantially devoid of water, or not, and the water formed during the reaction is substantially removed or retained in the reaction medium.

In an advantageous embodiment, the present invention relates to a process for the preparation of:
a p-(R-oxy)calixarene selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or
a mixture of at least two of said p-(R-oxy)calix[9-20]arenes in which said at least two p-(R-oxy)calixarenes are present in said mixture each at a level of at least 5 mol. %,
in which said phenol substituted in position 4 of formula (I) is in particular selected from 4-benzyloxyphenol or 4-octyloxyphenol, the initial reaction medium before the start of the reaction being in particular substantially devoid of water, the source of formaldehyde being in particular para-formaldehyde and the organic solvent being in particular xylene, the water formed in the reaction medium during said preparation of said compound being optionally substantially removed from said reaction medium, as defined above, in which said base is selected from sodium hydroxide or potassium hydroxide, in particular in an aqueous solution.

In an advantageous embodiment, the present invention relates to a process for the preparation of:
a p-(R-oxy)calixarene selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or
a mixture of said p-(R-oxy)calix[9-20]arenes,
in which said phenol substituted in position 4 of formula (I) is in particular selected from 4-benzyloxyphenol or 4-octyloxyphenol, the initial reaction medium before the start of the reaction being in particular substantially devoid of water, the source of formaldehyde being in particular para-formaldehyde and the organic solvent being in particular xylene, the water formed in the reaction medium during said preparation of said compound being optionally substantially removed from said reaction medium, in which said base is selected from sodium hydroxide or potassium hydroxide as defined above, in which said p-(R-oxy)calixarene or said mixture of said p-(R-oxy)calix[9-20]arenes also comprises a p-(R-oxy)calix[7]arene in the form of the sodium or potassium monosalt depending on the base used.

In this embodiment, the mixture of p-(R-oxy)calix[9-20]arenes obtained is in a minority (between 5 and 10 mol. %) and the reaction leads mainly to p-(R-oxy)calix[7]arene in the form of the sodium or potassium monosalt which can be isolated in this form between 50 and 95 mol. %.

In an advantageous embodiment, the present invention relates to a process for the preparation of:
a p-(R-oxy)calixarene selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or
a mixture of at least two of said p-(R-oxy)calix[9-20]arenes in which said at least two p-(R-oxy)calixarenes are present in said mixture each at a level of at least 5 mol. %,
in which said phenol substituted in position 4 of formula (I) is in particular selected from 4-benzyloxyphenol or 4-octyloxyphenol, the initial reaction medium before the start of the reaction being in particular substantially devoid of water, the source of formaldehyde being in particular para-formaldehyde and the organic solvent being in particular xylene, the water formed in the reaction medium during said preparation of said compound being optionally substantially removed from said reaction medium, in which said base is selected from sodium hydroxide or potassium hydroxide as defined above, in which said p-(R-oxy)calixarene or said mixture of said p-(R-oxy)calix[9-20]arenes also comprises a p-(R-oxy)calix[7]arene in the form of the sodium or potassium monosalt depending on the base used.

In an advantageous embodiment, the p-(R-oxy)calix[7]arene in the form of the sodium or potassium monosalt is p-(benzyloxy)calix[7]arene or p-(octyloxy)calix[7]arene.

In an advantageous embodiment, the present invention relates to one of the processes for the preparation of:
a p-(R-oxy)calixarene selected from a p-(R-oxy)calix[9]arene, a p-(R-oxy)calix[10]arene, a p-(R-oxy)calix[11]

arene, a p-(R-oxy)calix[12]arene, a p-(R-oxy)calix[13]
arene, a p-(R-oxy)calix[14]arene, a p-(R-oxy)calix[15]
arene, a p-(R-oxy)calix[16]arene, a p-(R-oxy)calix[17]
arene, a p-(R-oxy)calix[18]arene, a p-(R-oxy)calix[19]
arene, a p-(R-oxy)calix[20]arene, or
a mixture of said p-(R-oxy)calix[9-20]arenes,
as defined above, comprising the following stages:
a. bringing sodium hydroxide or potassium hydroxide, in particular in an aqueous solution, into contact with at least one phenol substituted in position 4 of formula (I), said base being at a total concentration comprised from more than 0.5 equivalent to 1.5 equivalent, advantageously from more than 0.5 equivalent to 1.2 equivalent, in particular equal to 0.6 equivalent, with respect to said at least one phenol substituted in position 4 of formula (I), of the paraformaldehyde in an organic solvent then heating,
in order to obtain:
a p-(R-oxy)calixarene selected from a p-(R-oxy)calix[9]
arene, a p-(R-oxy)calix[10]arene, a p-(R-oxy)calix[11]
arene, a p-(R-oxy)calix[12]arene, a p-(R-oxy)calix[13]
arene, a p-(R-oxy)calix[14]arene, a p-(R-oxy)calix[15]
arene, a p-(R-oxy)calix[16]arene, a p-(R-oxy)calix[17]
arene, a p-(R-oxy)calix[18]arene, a p-(R-oxy)calix[19]
arene, a p-(R-oxy)calix[20]arene, or,
a mixture of said p-(R-oxy)calixarenes,
and a p-(R-oxy)calix[7]arene,
in the salified form in the final reaction medium,
b. optionally filtration of the final reaction medium in order to obtain said p-(R-oxy)calix[7]arene in the form of the sodium or potassium monosalt, followed by an additional stage of neutralization of the p-(R-oxy)calix[7]arene in the form of the sodium or potassium monosalt in order to obtain the p-(R-oxy)calix[7]arene in the neutralized form and a filtered final reaction medium,
c. neutralization of said final reaction medium or of said filtered final reaction medium in order to obtain:
said p-(R-oxy)calixarene or said mixture, substantially devoid of p-(R-oxy)calix[7]arene, in the neutralized form, or
said p-(R-oxy)calixarene or said mixture, also comprising a p-(R-oxy)calix[7]arene, in the neutralized form,
d. optionally purification:
of said p-(R-oxy)calixarene or of said mixture, substantially devoid of p-(R-oxy)calix[7]arene, in the neutralized form, or
of said p-(R-oxy)calixarene or of said mixture, also comprising a p-(R-oxy)calix[7]arene, in the neutralized form,
in particular by crystallization from a mixture of solvents based on DMSO in order to obtain:
said p-(R-oxy)calixarene or said mixture, substantially devoid of p-(R-oxy)calix[7]arene, in the purified, neutralized form, or
said p-(R-oxy)calixarene or said mixture, also comprising a p-(R-oxy)calix[7]arene, in the purified, neutralized form.

In an advantageous embodiment, the present invention relates to one of the processes for the preparation of:
a p-(R-oxy)calixarene selected from a p-(R-oxy)calix[9]
arene, a p-(R-oxy)calix[10]arene, a p-(R-oxy)calix[11]
arene, a p-(R-oxy)calix[12]arene, a p-(R-oxy)calix[13]
arene, a p-(R-oxy)calix[14]arene, a p-(R-oxy)calix[15]
arene, a p-(R-oxy)calix[16]arene, a p-(R-oxy)calix[17]
arene, a p-(R-oxy)calix[18]arene, a p-(R-oxy)calix[19]
arene, a p-(R-oxy)calix[20]arene, or
a mixture of said p-(R-oxy)calix[9-20]arenes,
as defined above, comprising the following stages:
a. bringing sodium hydroxide or potassium hydroxide, in particular in an aqueous solution, into contact with at least one phenol substituted in position 4 of formula (I), said base being at a total concentration comprised from more than 0.5 equivalent to 1.5 equivalent, advantageously from more than 0.5 equivalent to 1.2 equivalent, in particular equal to 0.6 equivalent, with respect to said at least one phenol substituted in position 4 of formula (I), of paraformaldehyde in an organic solvent then heating,
in order to obtain:
a p-(R-oxy)calixarene selected from a p-(R-oxy)calix[9]
arene, a p-(R-oxy)calix[10]arene, a p-(R-oxy)calix[11]
arene, a p-(R-oxy)calix[12]arene, a p-(R-oxy)calix[13]
arene, a p-(R-oxy)calix[14]arene, a p-(R-oxy)calix[15]
arene, a p-(R-oxy)calix[16]arene, a p-(R-oxy)calix[17]
arene, a p-(R-oxy)calix[18]arene, a p-(R-oxy)calix[19]
arene, a p-(R-oxy)calix[20]arene, or,
a mixture of at least two of said p-(R-oxy)calixarenes in which said at least two p-(R-oxy)calixarenes are present in said mixture each at a level of at least 5 mol. %, and a p-(R-oxy)calix[7]arene,
in the salified form in the final reaction medium,
b. optionally filtration of the final reaction medium in order to obtain said p-(R-oxy)calix[7]arene in the form of the sodium or potassium monosalt, followed by an additional stage of neutralization of the p-(R-oxy)calix[7]arene in the form of the sodium or potassium monosalt in order to obtain the p-(R-oxy)calix[7]arene in the neutralized form and a filtered final reaction medium,
c. neutralization of said final reaction medium or of said filtered final reaction medium in order to obtain:
said p-(R-oxy)calixarene or said mixture, substantially devoid of p-(R-oxy)calix[7]arene, in the neutralized form, or
said p-(R-oxy)calixarene or said mixture, also comprising a p-(R-oxy)calix[7]arene, in the neutralized form,
d. optionally purification:
of said p-(R-oxy)calixarene or of said mixture, substantially devoid of p-(R-oxy)calix[7]arene, in the neutralized form, or
of said p-(R-oxy)calixarene or of said mixture, also comprising a p-(R-oxy)calix[7]arene, in the neutralized form,
in particular by crystallization from a mixture of solvents based on DMSO in order to obtain:
said p-(R-oxy)calixarene or said mixture, substantially devoid of p-(R-oxy)calix[7]arene, in the purified neutralized form, or
said p-(R-oxy)calixarene or said mixture, also comprising a p-(R-oxy)calix[7]arene, in the purified, neutralized form.

By "substantially devoid of p-(R-oxy)calix[7]arene", is meant that said mixture comprises less than 5 mol. % of p-(R-oxy)calix[7]arene. In stage a., the potassium hydroxide or sodium hydroxide used can be in an aqueous solution or solid. When the potassium hydroxide or sodium hydroxide are in an aqueous solution, the concentration thereof is advantageously comprised from 10% to 50% by weight.

The source of formaldehyde can be aqueous or non-aqueous, in particular in the non-aqueous form and in particular it corresponds to paraformaldehyde.

The initial reaction medium can therefore be substantially devoid of water or not.

The organic solvent denotes any non-polar solvent the boiling point of which is greater than approximately 50° C., in particular a solvent the boiling point of which is comprised from 50 to 250° C., in particular xylene, toluene, octane, diphenyl ether, mesitylene, chlorobenzene, dichlorobenzene, trichlorobenzene, in particular the organic solvent is xylene.

The heating is comprised from 50° C. to 250° C., in particular it is carried out at the boiling point of the organic solvent used, for a period of time comprised from 3 h to 15 h in order to obtain said p-(R-oxy)calix[n]arene in which n is comprised from 9 to 20 or said mixture in the salified form, and said p-(R-oxy)calix[7]arene in the final reaction medium.

The water formed in the reaction medium during the reaction can be removed by techniques well known to a person skilled in the art, for example by means of a Dean-Stark device or flushing the reaction medium with a neutral gas, in particular nitrogen or argon.

In stage b., which is optional, the p-(R-oxy)calix[7]arene in the form of the sodium or potassium salt, which is in the form of a precipitate, is isolated by filtration and the filtrate then contains said p-(R-oxy)calix[n]arene in which n is comprised from 9 to 20 or said mixture in the salified form.

In stage c., the neutralization is carried out with an acid, in particular in an aqueous solution, in particular with hydrochloric acid, nitric acid, or sulphuric acid.

It leads to a compound comprising said p-(R-oxy)calix[n]arene in which n is comprised from 9 to 20 or said mixture in the neutralized form, and also comprising said p-(R-oxy)calix[7]arene in the neutralized form if the neutralization has been carried out without the filtration of stage b. above.

The p-(R-oxy)calix[7]arene in the form of the sodium or potassium salt can in turn be neutralized by means of an acid as defined in stage c. in order to produce p-(R-oxy)calix[7]arene in the neutralized form.

Advantageously, the formaldehyde used is paraformaldehyde, the sodium hydroxide and/or potassium hydroxide are in the aqueous form, the solvent used is xylene and the reaction time is approximately 15 h.

In stage d., the purification when it is carried out, consists of a crystallization from a solvent mixture based on an aprotic polar solvent, in particular based on DMSO or DMF, and in particular a DMSO/toluene or DMSO/acetone mixture, the DMSO being in a proportion of 5% to 50% by volume in the mixture of solvent, in particular 10% by volume with respect to the second solvent, optionally followed by chromatography.

The second solvent can also be a toluene/acetone solvent mixture irrespective of the proportion of each of the two solvents.

In an advantageous embodiment, the reaction time of stage a. defined above is comprised from 30 min to 1 h in order to obtain firstly oligomers constituted by phenolic units then, secondly, the dimer of formula (II) defined above, in the salified form, virtually quantitatively, which after said neutralization of said stage b. is obtained in the neutralized form.

When the heating is continued with the salified dimer, the calixarenes of the invention are then formed.

In an advantageous embodiment of the sodium hydroxide or potassium hydroxide process, the R group represents a benzyl or an octyl.

According to another aspect, the present invention relates to a phenolic dimer substituted in position 4 of following formula (II) as novel products:

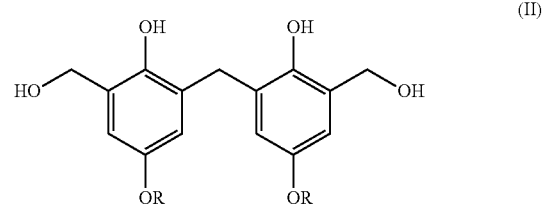

in which R is as defined in formula (I) above.

In an advantageous embodiment, the present invention relates to p-(R-oxy)calix[7]arene in the form of the sodium or potassium monosalt, in particular p-(octyloxy)calix[7]arene in the form of the sodium or potassium monosalt or p-(benzyloxy)calix[7]arene in the form of the sodium or potassium monosalt.

These two compounds in the form of sodium or of potassium salts are novel products.

In an advantageous embodiment, the present invention relates to a phenolic dimer, in which R is selected from the benzyl group or the octyl group.

According to another aspect, the present invention relates to a p-(R-oxy)calixarene or a mixture of p-(R-oxy)calix[9-20]arenes of following formula (III) as novel products:

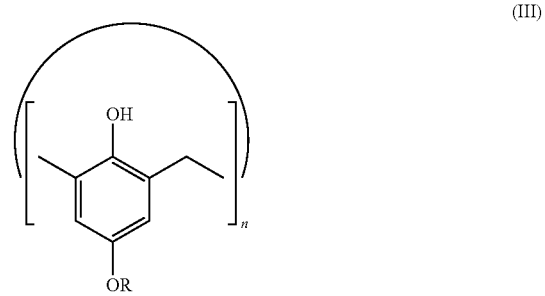

in which n is an integer comprised from 9 to 20, R being as defined in formula (I) above.

The p-(R-oxy)calix[n]arene in which n is an integer comprised from 9 to 20, therefore corresponds to a compound selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or a mixture thereof comprising at least two p-(R-oxy)calix[9-20]arenes from the twelve defined above.

Each p-(R-oxy)calix[n]arene present in said mixture, in which n is an integer comprised from 9 to 20, can be in a proportion range comprised from 0 to 100% provided that at least two p-(R-oxy)calix[n]arenes in which n is an integer comprised from 9 to 20 are present in a proportion greater than 0.

The present invention also relates to a p-(R-oxy)calixarene or a mixture of at least two p-(R-oxy)calix[9-20]arenes in which said at least two p-(R-oxy)calixarenes are present in said mixture each at a level of at least 5 mol. % of following formula (III) as novel products:

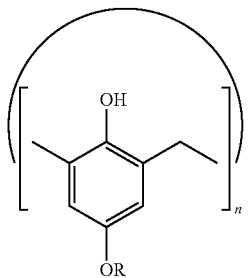

(III)

in which n is an integer comprised from 9 to 20, R being as defined in formula (I) above.

In particular, the p-(R-oxy)calix[n]arene in which n is an integer comprised from 9 to 20, therefore corresponds to a compound selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or a mixture thereof comprising at least two p-(R-oxy)calix[9-20] arenes from the twelve defined above, in which said at least two p-(R-oxy)calixarenes are present in said mixture each at a level of at least 5 mol. %.

Thus, the at least two p-(R-oxy)calix[n]arenes present in said mixture, in which n is an integer comprised from 9 to 20, can each be in a proportion range comprised from 5 to 95%.

In another advantageous embodiment, the present invention relates to a p-(R-oxy)calix[n]arene in which n is an integer comprised from 9 to 20 or a mixture of p-(R-oxy)calix[9-20]arenes, as defined above, in which R is selected from the benzyl group or the octyl group.

In another advantageous embodiment, the mixture of p-(R-oxy)calix[9-20]arenes obtained is constituted mainly by p-(R-oxy)calix[9]arene, p-(R-oxy)calix[10]arene, p-(R-oxy)calix[12]arene, p-(R-oxy)calix[13]arene, p-(R-oxy)calix[16]arene, in particular the mixture corresponds to a mixture of p-(benzyloxy)calix[9-20]arenes constituted mainly by p-(benzyloxy)calix[9]arene, p-(benzyloxy)calix[10]arene, p-(benzyloxy)calix[12]arene, p-(benzyloxy)calix[13]arene, p-(benzyloxy)calix[16]arene or of p-(octyloxy)calix[9-20] arenes constituted mainly by p-(octyloxy)calix[9]arene, p-(octyloxy)calix[10]arene, p-(octyloxy)calix[12]arene, p-(octyloxy)calix[13]arene, p-(octyloxy)calix[16]arene.

In another advantageous embodiment, the mixture of p-(benzyloxy)calix[9-20]arenes obtained is constituted mainly by p-(benzyloxy)calix[9]arene, p-(benzyloxy)calix[10]arene, p-(benzyloxy)calix[12]arene, p-(benzyloxy)calix[13]arene, p-(benzyloxy)calix[16]arene or by p-(octyloxy)calix[9-20]arenes constituted mainly by p-(octyloxy)calix[9]arene, p-(octyloxy)calix[10]arene, p-(octyloxy)calix[12]arene, p-(octyloxy)calix[13]arene, p-(octyloxy)calix[16]arene and also comprises p-(R-oxy)calix[5]arene, in particular p-(benzyloxy)calix[5]arene or p-(octyloxy)calix[5]arene in a proportion of approximately 10% by weight.

According to another aspect, the present invention relates to a p-(R-oxy)calix[5]arene, in particular p-(benzyloxy)calix[5]arene or p-(octyloxy)calix[5]arene.

p-(Benzyloxy)calix[5]arene or p-(octyloxy)calix[5]arene can easily be obtained by purification of the mixture containing it defined above.

In an advantageous embodiment, the present invention relates to a p-(R-oxy)calix[n]arene in which n is an integer comprised from 9 to 20 or a mixture of p-(R-oxy)calix[9-20] arenes, as defined above, R being in particular selected from the benzyl group or the octyl group, also comprising a p-(R-oxy)calix[7]arene, in particular p-(benzyloxy)calix[7]arene or p-(octyloxy)calix[7]arene.

The proportion of p-(R-oxy)calix[7]arene present with the p-(R-oxy)calix[n]arene in which n is an integer comprised from 9 to 20 or with a mixture of p-(R-oxy)calix[9-20]arene is variable and is comprised from more than 0% to 99.1% by weight.

In this embodiment, the p-(R-oxy)calix[7]arene can be in the salified form or non-salified form.

In another advantageous embodiment, the present invention relates to a p-(R-oxy)calix[n]arene in which n is an integer comprised from 9 to 20 or a mixture of p-(R-oxy)calix[9-20]arenes, R being in particular selected from the benzyl group or the octyl group, as defined above, also comprising a p-(R-oxy)calix[7]arene in the form of the sodium or potassium monosalt.

The proportion of p-(R-oxy)calix[7]arene in the salified form present with the p-(R-oxy)calix[n]arene in which n is an integer comprised from 9 to 20 or with a mixture of p-(R-oxy)calix[9-20]arene is variable and is comprised from more than 0% to 99.1% by weight.

In another advantageous embodiment, the present invention relates to the p-(R-oxy)calix[7]arene in the form of the sodium or potassium monosalt, in particular p-(benzyloxy)calix[7]arene or p-(octyloxy)calix[7]arene in the form of the sodium or potassium monosalt.

The p-(R-oxy)calix[7]arene, in particular p-(benzyloxy)calix[7]arene or p-(octyloxy)calix[7]arene in the form of the sodium or potassium monosalt, can easily be obtained by filtration of the final reaction medium of the mixture containing them defined above.

According to another aspect, the present invention relates to the use of a p-(R-oxy)calixarene selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or of a mixture of said p-(R-oxy)calix[9-20]arenes, for the constitution of a material or in the context of the mechanical reinforcement of materials.

The present invention also relates to the use of a p-(R-oxy)calixarene selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or of a mixture of at least two of said p-(R-oxy)calix[9-20]arenes, for the constitution of a material or in the context of the mechanical reinforcement of materials in which said at least two p-(R-oxy)calixarenes are present in said mixture each at a level of at least 5 mol. %.

The p-(R-oxy)calix[n]arene in which n is comprised from 9 to 20 or the mixture of said p-(R-oxy)calix[9-20]arenes can also be used for trapping particles, the synthesis of metallic particles with controlled dimensions and a low dispersion, nanofiltration, gas filtration, the complexing of ions, the vectorization and encapsulation of molecules. The large cavity present within the large calixarenes also makes it possible to envisage the formation of cross-linked or non-cross-linked porous materials, having gel or foam applications.

The present invention also relates to the use of a p-(R-oxy)calixarene selected from a p-(R-oxy)calix[9]arene, a p-(R- oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or of a mixture of said p-(R-oxy)calix[9-20]arenes, for the constitution of a material, for example a cross-linked or non-cross-linked porous material, said material being able to be used in the implementation of a process for obtaining gels or foams, for the constitution of a material in the context of the mechanical reinforcement of materials, for the synthesis of metallic particles with controlled dimensions and a low dispersion, for nanofiltration, for gas filtration, for the complexing of ions, for the vectorization or encapsulation of molecules.

The present invention also relates to the use of a p-(R-oxy)calixarene selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or of a mixture of at least two of said p-(R-oxy)calix[9-20]arenes in which said at least two p-(R-oxy)calixarenes are present in said mixture each at a level of at least 5 mol. %, for the constitution of a material, for example a cross-linked or non-cross-linked porous material, said material being able to be used in the implementation of a process for obtaining gels or foams, for the constitution of a material in the context of the mechanical reinforcement of materials, for the synthesis of metallic particles with controlled dimensions and a low dispersion, for nanofiltration, for gas filtration, for the complexing of ions, for the vectorization or encapsulation of molecules.

In an embodiment, the present invention relates to the use of a p-(R-oxy)calixarene selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or of a mixture of said p-(R-oxy)calix[9-20]arenes, as defined above in which said p-(R-oxy)calixarene or said mixture also comprises a p-(R-oxy)calix[7]arene.

In an embodiment, the present invention relates to the use of a p-(R-oxy)calixarene selected from a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, or of a mixture of at least two of said p-(R-oxy)calix[9-20]arenes in which said at least two p-(R-oxy)calixarenes are present in said mixture each at a level of at least 5 mol. %, as defined above in which said p-(R-oxy)calixarene or said mixture also comprises a p-(R-oxy)calix[7]arene.

The p-(R-oxy)calix[7]arene can be in the form of the sodium or potassium salt or neutral.

In an advantageous embodiment, the R group of said p-(R-oxy)calix[n]arene, in which n is comprised from 9 to 20 or of said mixture of said p-(R-oxy)calix[9-20]arenes used with or without p-(R-oxy)calix[7]arene, is a benzyl or an octyl.

According to yet another aspect, the present invention relates to the use of a p-(R-oxy)calixarene or of a mixture of p-(R-oxy)calixarenes as defined above, capable of being obtained by one of the processes defined above, for the constitution of a material or in the context of the mechanical reinforcement of materials.

According to yet another aspect, the p-(R-oxy)calixarene or the mixture of p-(R-oxy)calixarenes as defined above, capable of being obtained by one of the processes defined above, can also be used for trapping particles, the synthesis of metallic particles with controlled dimensions and a low dispersion, nanofiltration, gas filtration, complexing of ions, vectorization and encapsulation of molecules. The large cavity present within the large calixarenes also makes it possible to envisage the formation of cross-linked or non-cross-linked porous materials, having gel or foam applications.

According to yet another aspect, the present invention relates to the use of a p-(R-oxy)calixarene or of a mixture of p-(R-oxy)calixarenes as defined above, capable of being obtained by one of the processes defined above, for the constitution of a material, for example a cross-linked or non-cross-linked porous material, said material being able to be used in the implementation of a process for obtaining gels or foams, for the constitution of a material in the context of the mechanical reinforcement of materials, for the synthesis of metallic particles with controlled dimensions and a low dispersion, for nanofiltration, for gas filtration, for the complexing of ions, for the vectorization or encapsulation of molecules.

The present invention also relates to the use of at least one base, said base being rubidium hydroxide, with a phenol of formula (I), said base being at a total concentration greater than or equal to 0.3 equivalent and less than or equal to 0.5 equivalent with respect to said phenol of formula (I), for the preparation of a mixture comprising p-(R-oxy)calix[6]arene, p-(R-oxy)calix[7]arene and p-(R-oxy)calix[8]arene and a mixture of p-(R-oxy)calix[9-20]arenes.

The present invention also relates to the use of at least one base, said base being rubidium hydroxide, with p-(benzyloxy)phenol, said base being at a total concentration greater than or equal to 0.3 equivalent and less than or equal to 0.5 equivalent with respect to said p-(benzyloxy)phenol, for the preparation of a mixture comprising p-(benzyloxy)calix[6]arene, p-(benzyloxy)calix[7]arene and p-(benzyloxy)calix[8]arene and a mixture of p-(benzyloxy)calix[9-20]arenes.

The Inventors have surprisingly found that the combination of at least one base, said base being rubidium hydroxide, and a total concentration greater than or equal to 0.3 equivalent and less than or equal to 0.5 equivalent with respect to said phenol of formula (I) made it possible to obtain a mixture of p-(R-oxy)calix[9-20]arenes, at 50% or more, whereas the mixture of p-(R-oxy)calix[6]arene and p-(R-oxy)calix[7]arene also obtained is in a minority or equal to 50% at most.

The Inventors have surprisingly found that the combination of at least one base, said base being rubidium hydroxide, and a total concentration greater than or equal to 0.3 equivalent and less than or equal to 0.5 equivalent with respect to the p-(benzyloxy)phenol made it possible to obtain a mixture of p-(benzyloxy)calix[9-20]arenes, at 50% or more, whereas the mixture of p-(benzyloxy)calix[6]arene and p-(benzyloxy)calix[7]arene, also obtained is in a minority or equal to 50% at most.

According to another aspect, the present invention relates to a process for the preparation of a compound consisting of a mixture comprising a mixture of p-(R-oxy)calix[9-20]arenes, p-(R-oxy)calix[6]arene, p-(R-oxy)calix[7]arene and p-(R-oxy)calix[8]arene, comprising a stage of bringing rubidium hydroxide into contact with a phenol of formula (I) and paraformaldehyde, said base being at a total concentration greater than or equal to 0.3 equivalent and less than or equal to 0.5 equivalent with respect to said phenol of formula (I).

According to another aspect, the present invention relates to a process for the preparation of a compound consisting of a mixture comprising a mixture of p-(benzyloxy)calix[9-20]arenes, p-(benzyloxy)calix[6]arene, p-(benzyloxy)calix[7]arene and p-(benzyloxy)calix[8]arene, comprising a stage of bringing rubidium hydroxide into contact with p-(benzyloxy)phenol and paraformaldehyde, said a base being at a total concentration greater than or equal to 0.3 equivalent and less than or equal to 0.5 equivalent with respect to said p-(benzyloxy)phenol.

According to another aspect, the present invention relates to a process for the preparation of a compound consisting of a mixture comprising a mixture of p-(R-oxy)calix[9-20]arenes, p-(R-oxy)calix[6]arene, p-(R-oxy)calix[7]arene and p-(R-oxy)calix[8]arene, comprising a stage of bringing rubidium hydroxide into contact with a phenol of formula (I) and paraformaldehyde, in which said base is at a total concentration greater than or equal to 0.3 equivalent and less than or equal to 0.5 equivalent, in order to obtain a mixture comprising a mixture of p-(R-oxy)calix[9-20]arenes, p-(R-oxy)calix[6]arene, p-(R-oxy)calix[7]arene and p-(R-oxy)calix[8]arene in the salified form. Quite unexpectedly, the Inventors have found that the use of rubidium hydroxide at a total concentration greater than or equal to 0.3 equivalent and less than or equal to 0.5 equivalent made it possible to obtain a mixture comprising as a majority, i.e. in a proportion of 50% or more by weight, a mixture of p-(R-oxy)calix[9-20]arenes in the salified form, as well as p-(R-oxy)calix[6]arene, p-(R-oxy)calix[7]arene and p-(R-oxy)calix[8]arene in the salified form as a minority.

According to another aspect, the present invention relates to a process for the preparation of a compound consisting of a mixture comprising a mixture of p-(R-oxy)calix[9-20]arenes, p-(R-oxy)calix[6]arene, p-(R-oxy)calix[7]arene and p-(R-oxy)calix[8]arene, in particular a mixture of p-(benzyloxy)calix[9-20]arenes, p-(benzyloxy)calix[6]arene, p-(benzyloxy)calix[7]arene and p-(benzyloxy)calix[8]arene, comprising a stage of bringing rubidium hydroxide into contact with p-(benzyloxy)phenol and paraformaldehyde, in which said base is at a total concentration greater than or equal to 0.3 equivalent and less than or equal to 0.5 equivalent, in order to obtain a mixture comprising a mixture of p-(benzyloxy)calix[9-20]arenes, p-(benzyloxy)calix[6]arene, p-(benzyloxy)calix[7]arene and p-(benzyloxy)calix[8]arene in the salified form. Quite unexpectedly, the Inventors have found that the use of rubidium hydroxide at a total concentration greater than or equal to 0.3 equivalent and less than or equal to 0.5 equivalent made it possible to obtain a mixture comprising as a majority, i.e. in a proportion of 50% or more by weight, a mixture of p-(benzyloxy)calix[9-20]arenes in the salified form, as well as p-(benzyloxy)calix[6]arene, p-(benzyloxy)calix[7]arene and p-(benzyloxy)calix[8]arene in the salified form as a minority.

In an advantageous embodiment, the total concentration of rubidium hydroxide is 0.30 equivalent, or 0.31 equivalent, or 0.32 equivalent, or 0.33 equivalent, or 0.34 equivalent, or 0.35 equivalent, or 0.36 equivalent, or 0.37 equivalent, or 0.38 equivalent, or 0.39 equivalent, or 0.40 equivalent, or 0.41 equivalent, or 0.42 equivalent, or 0.43 equivalent, or 0.44 equivalent, or 0.45 equivalent, or 0.46 equivalent, or 0.47 equivalent, or 0.48 equivalent, or 0.49 equivalent, or 0.50 equivalent.

In an advantageous embodiment, the present invention relates to a process for the preparation of a compound consisting of a mixture comprising a mixture of p-(R-oxy)calix[9-20]arenes, p-(R-oxy)calix[6]arene, p-(R-oxy)calix[7]arene and p-(R-oxy)calix[8]arene, comprising a stage of bringing rubidium hydroxide into contact with a phenol of formula (I) and paraformaldehyde, in which said base is at a total concentration greater than or equal to 0.3 equivalent and less than or equal to 0.5 equivalent, in order to obtain a mixture comprising a mixture of p-(R-oxy)calix[9-20]arenes, p-(R-oxy)calix[6]arene, p-(R-oxy)calix[7]arene and p-(R-oxy)calix[8]arene, in the salified form, as defined above, comprising an additional stage of neutralization of the mixture comprising a mixture of p-(R-oxy)calix[9-20]arenes, p-(R-oxy)calix[6]arene, p-(R-oxy)calix[7]arene and p-(R-oxy)calix[8]arene, in the neutralized form.

In an advantageous embodiment, the present invention relates to a process for the preparation of a compound consisting of a mixture comprising a mixture of p-(benzyloxy)calix[9-20]arenes, p-(benzyloxy)calix[6]arene, p-(benzyloxy)calix[7]arene and p-(benzyloxy)calix[8]arene, comprising a stage of bringing rubidium hydroxide into contact with p-(benzyloxy)phenol and paraformaldehyde, in which said base is at a total concentration greater than or equal to 0.3 equivalent and less than or equal to 0.5 equivalent, in order to obtain a mixture comprising a mixture of p-(benzyloxy)calix[9-20]arenes, p-(benzyloxy)calix[6]arene, p-(benzyloxy)calix[7]arene and p-(benzyloxy)calix[8]arene, in the salified form, as defined above, comprising an additional stage of neutralization of the mixture comprising a mixture of p-(benzyloxy)calix[9-20]arenes, p-(benzyloxy)calix[6]arene, p-(benzyloxy)calix[7]arene and p-(benzyloxy)calix[8]arene, in the neutralized form.

In an advantageous embodiment, the present invention relates to a process for the preparation of a compound consisting of a mixture comprising a mixture of p-(R-oxy)calix[9-20]arenes, p-(R-oxy)calix[6]arene, p-(R-oxy)calix[7]arene and p-(R-oxy)calix[8]arene, comprising a stage of bringing rubidium hydroxide into contact with a phenol of formula (I) and paraformaldehyde, in which said base is at a total concentration greater than or equal to 0.3 equivalent and less than or equal to 0.5 equivalent, in order to obtain a mixture comprising a mixture of p-(R-oxy)calix[9-20]arenes, p-(R-oxy)calix[6]arene, p-(R-oxy)calix[7]arene and p-(R-oxy)calix[8]arene, in the salified form, comprising an additional stage of neutralization of the mixture comprising a mixture of p-(R-oxy)calix[9-20]arenes, p-(R-oxy)calix[6]arene, p-(R-oxy)calix[7]arene and p-(R-oxy)calix[8]arene, obtained in the salified form in order to obtain a mixture comprising a mixture of p-(R-oxy)calix[9-20]arenes, p-(R-oxy)calix[6]arene, p-(R-oxy)calix[7]arene and p-(R-oxy)calix[8]arene, in the neutralized form, as defined above, comprising an additional stage of crystallization of the mixture comprising a mixture of p-(R-oxy)calix[9-20]arenes, p-(R-oxy)calix[6]arene, p-(R-oxy)calix[7]arene and p-(R-oxy)calix[8]arene, in the neutralized form, from a mixture of solvents based on DMSO in order to obtain p-(R-oxy)calix[6]arene in the neutralized form.

In an advantageous embodiment, the present invention relates to a process for the preparation of a compound consisting of a mixture comprising a mixture of p-(benzyloxy)calix[9-20]arenes, p-(benzyloxy)calix[6]arene, p-(benzyloxy)calix[7]arene and p-(benzyloxy)calix[8]arene, comprising a stage of bringing rubidium hydroxide into contact with p-(benzyloxy)phenol and paraformaldehyde, in which said base is at a total concentration greater than or equal to 0.3 equivalent and less than or equal to 0.5 equivalent, in order to obtain a mixture comprising a mixture of p-(benzyloxy)calix[9-20]arenes, p-(benzyloxy)calix[6]

arene, p-(benzyloxy)calix[7]arene and p-(benzyloxy)calix[8]arene, in the salified form, comprising an additional stage of neutralization of the mixture comprising a mixture of p-(benzyloxy)calix[9-20]arenes, p-(benzyloxy)calix[6]arene, p-(benzyloxy)calix[7]arene and p-(benzyloxy)calix[8]arene, obtained in the salified form, in order to obtain a mixture comprising a mixture of p-(benzyloxy)calix[9-20]arenes, p-(benzyloxy)calix[6]arene, p-(benzyloxy)calix[7]arene and p-(benzyloxy)calix[8]arene, in the neutralized form, as defined above,
comprising an additional stage of crystallization of the mixture comprising a mixture of p-(benzyloxy)calix[9-20]arenes, p-(benzyloxy)calix[6]arene, p-(benzyloxy)calix[7]arene and p-(benzyloxy)calix[8]arene, in the neutralized form, from a mixture of solvents based on DMSO in order to obtain p-(benzyloxy)calix[6]arene in the neutralized form.

The Inventors also found that the treatment of the mixture comprising a mixture of p-(R-oxy)calix[9-20]arenes, p-(R-oxy)calix[6]arene, p-(R-oxy)calix[7]arene and p-(R-oxy)calix[8]arene, in the neutralized form in a mixture of solvents based on DMSO, made it possible to isolate the mixture of p-(R-oxy)calix[9-20]arenes, with an excellent yield, greater than or equal to 50%, in contrast to the prior art.

The Inventors also found that the treatment of the mixture comprising a mixture of p-(benzyloxy)calix[9-20]arenes, p-(benzyloxy)calix[6]arene, p-(benzyloxy)calix[7]arene and p-(benzyloxy)calix[8]arene, in the neutralized form, in a mixture of solvents based on DMSO made it possible to isolate the mixture of p-(benzyloxy)calix[9-20]arenes, with an excellent yield, greater than or equal to 50%, in contrast to the prior art.

By the expression "DMSO-based solvent", is meant a solvent mixture comprising at least 10% by volume of DMSO.

The DMSO makes it possible to solubilize the colloid formed by the mixture comprising p-(R-oxy)calix[6]arene, p-(R-oxy)calix[7]arene and p-(R-oxy)calix[8]arene, in particular the mixture comprising p-(benzyloxy)calix[6]arene, p-(benzyloxy)calix[7]arene and p-(benzyloxy)calix[8]arene in the neutralized form.

In an advantageous embodiment, the present invention relates to a process for the preparation of a compound consisting of a mixture comprising a mixture of p-(R-oxy)calix[9-20]arenes, p-(R-oxy)calix[6]arene, p-(R-oxy)calix[7]arene and p-(R-oxy)calix[8]arene, as defined above, comprising the following stages:
  a. bringing rubidium hydroxide at a total concentration greater than or equal to 0.3 equivalent and less than or equal to 0.5 equivalent, into contact with a phenol of formula (I) and formaldehyde, in a solvent, then heating in order to obtain a mixture comprising a mixture of p-(R-oxy)calix[9-20]arenes, p-(R-oxy)calix[6]arene, p-(R-oxy)calix[7]arene and p-(R-oxy)calix[8]arene in the salified form,
  b. neutralization of said mixture comprising a mixture of p-(R-oxy)calix[9-20]arenes, p-(R-oxy)calix[6]arene, p-(R-oxy)calix[7]arene and p-(R-oxy)calix[8]arene in the neutralized form,
  optionally, crystallization of the mixture comprising p-(R-oxy)calix[6]arene and p-(R-oxy)calix[7]arene in the neutralized form from a mixture of solvents based on DMSO in order to obtain the mixture of p-(R-oxy)calix[9-20]arenes in the neutralized form.

The solvent of stage a. is a solvent with a high boiling point comprised from approximately 100 to approximately 200° C., in particular approximately 140° C., for example xylene, but without being limited thereto.

The heating therefore depends partly on the nature of the solvent and can be carried out from 30° C. to 200° C.

Stage a. leads to a mixture comprising a mixture of p-(R-oxy)calix[9-20]arenes, p-(R-oxy)calix[6]arene, p-(R-oxy)calix[7]arene and p-(R-oxy)calix[8]arene, in the salified form.

The neutralization of the mixture is carried out with an acid, for example aqueous hydrochloric acid or aqueous sulphuric acid.

In an advantageous embodiment, the present invention relates to a process for the preparation of a compound consisting of a mixture comprising a mixture of p-(benzyloxy)calix[9-20]arenes, p-(benzyloxy)calix[6]arene, p-(benzyloxy)calix[7]arene and p-(benzyloxy)calix[8]arene, as defined above, comprising the following stages:
bringing rubidium hydroxide at a total concentration greater than or equal to 0.3 equivalent and less than or equal to 0.5 equivalent, into contact with p-(benzyloxy)phenol and formaldehyde, in a solvent, then heating in order to obtain a mixture comprising a mixture of p-(benzyloxy)calix[9-20]arenes, p-(benzyloxy)calix[6]arene, p-(benzyloxy)calix[7]arene and p-(benzyloxy)calix[8]arene in the salified form,
  a. neutralization of said mixture comprising a mixture of p-(benzyloxy)calix[9-20]arenes, p-(benzyloxy)calix[6]arene, p-(benzyloxy)calix[7]arene and p-(benzyloxy)calix[8]arene in the neutralized form,
  b. optionally, crystallization of the mixture comprising p-(benzyloxy)calix[6]arene and p-(benzyloxy)calix[7]arene, in the neutralized form, from a mixture of solvents based on DMSO, in order to obtain the mixture of p-(benzyloxy)calix[9-20]arenes in the neutralized form.

Stage a. leads to a mixture comprising a mixture of p-(benzyloxy)calix[9-20]arenes, p-(benzyloxy)calix[6]arene, p-(benzyloxy)calix[7]arene and p-(benzyloxy)calix[8]arene, in the salified form.

In an advantageous embodiment, the present invention relates to a process for the preparation of a compound consisting of a mixture comprising a mixture of p-(R-oxy)calix[9-20]arenes, p-(R-oxy)calix[6]arene, p-(R-oxy)calix[7]arene and p-(R-oxy)calix[8]arene, as defined above, comprising the following stages:
  a. bringing rubidium hydroxide at a total concentration greater than or equal to 0.3 equivalent and less than or equal to 0.5 equivalent, into contact with a phenol of formula (I) and formaldehyde, in a solvent, then heating in order to obtain a mixture comprising a mixture of p-(R-oxy)calix[9-20]arenes, p-(R-oxy)calix[6]arene, p-(R-oxy)calix[7]arene and p-(R-oxy)calix[8]arene, in the salified form,
  b. neutralization of said mixture comprising a mixture of p-(R-oxy)calix[9-20]arenes, p-(R-oxy)calix[6]arene, p-(R-oxy)calix[7]arene and p-(R-oxy)calix[8]arene, in the neutralized form,
  crystallization of said mixture comprising a mixture of p-(R-oxy)calix[9-20]arenes, p-(R-oxy)calix[6]arene, p-(R-oxy)calix[7]arene and p-(R-oxy)calix[8]arene, in the neutralized form, from a mixture of solvents based on DMSO in order to obtain the mixture of p-(R-oxy)calix[9-20]arenes in the neutralized form.

In an advantageous embodiment, the present invention relates to a process for the preparation of a compound consisting of a mixture comprising a mixture of p-(benzyloxy)calix[9-20]arenes, p-(benzyloxy)calix[6]arene, p-(benzyloxy)calix[7]arene and p-(benzyloxy)calix[8]arene, as defined above, comprising the following stages:
  c. bringing rubidium hydroxide at a total concentration greater than or equal to 0.3 equivalent and less than or equal to 0.5 equivalent, into contact with p-(benzyloxy) phenol and formaldehyde, in a solvent, then heating in order to obtain a mixture comprising a mixture of p-(benzyloxy)calix[9-20]arenes, p-(benzyloxy)calix[6] arene, p-(benzyloxy)calix[7]arene and p-(benzyloxy) calix[8]arene, in the salified form, d. neutralization of said mixture comprising a mixture of p-(benzyloxy)calix[9-20]arenes, p-(benzyloxy)calix[6] arene, p-(benzyloxy)calix[7]arene and p-(benzyloxy) calix[8]arene, in the neutralized form, e. crystallization of said mixture comprising a mixture of p-(benzyloxy)calix[9-20]arenes, p-(benzyloxy)calix[6] arene, p-(benzyloxy)calix[7]arene and p-(benzyloxy) calix[8]arene, in the neutralized form, from a mixture of solvents based on DMSO in order to obtain the mixture of p-(benzyloxy)calix[9-20]arenes in the neutralized form.

In an advantageous embodiment, the present invention relates to a process for the preparation of a compound consisting of a mixture comprising a mixture of p-(R-oxy)calix [9-20]arene s, p-(R-oxy)calix[6]arene, p-(R-oxy)calix[7] arene and p-(R-oxy)calix[8]arene, comprising bringing rubidium hydroxide at a total concentration greater than or equal to 0.3 equivalent and less than or equal to 0.5 equivalent, into contact with a phenol of formula (I) and formaldehyde, as defined above, in which the heating is carried out under reflux of the solvent, in particular xylene.

In an advantageous embodiment, the present invention relates to a process for the preparation of a compound consisting of a mixture comprising: 1) a mixture of p-(benzyloxy)calix[9-20]arene s, 2) p-(benzyloxy)calix[6]arene, 3) p-(benzyloxy)calix[7]arene and p-(benzyloxy)calix[8]arene, comprising bringing rubidium hydroxide at a total concentration greater than or equal to 0.3 equivalent and less than or equal to 0.5 equivalent, into contact with p-(benzyloxy)phenol and formaldehyde, as defined above, in which the heating is carried out under reflux of the solvent, in particular xylene.

In an advantageous embodiment, the present invention relates to a process for the preparation of a compound consisting of a mixture comprising p-(R-oxy)calix[6]arene and p-(R-oxy)calix[7]arene, or of a compound consisting of p-(R-oxy)calix[6]arene or p-(R-oxy)calix[7]arene comprising bringing rubidium hydroxide at a total concentration greater than or equal to 0.3 equivalent and less than or equal to 0.5 equivalent, into contact with a phenol of formula (I) and formaldehyde, as defined above, in which the mixture of solvents of the crystallization stage comprises DMSO and a polar solvent such as acetone.

By polar solvent, is meant a solvent having a dipole moment.

The DMSO are mixed with a polar solvent such as acetone in a proportion of 10% to 90% by volume.

The precipitate obtained corresponds to the purified mixture of p-(R-oxy)calix[9-20]arenes.

In an advantageous embodiment, the present invention relates to a process for the preparation of a compound consisting of a mixture comprising p-(benzyloxy)calix[6]arene and p-(benzyloxy)calix[7]arene, or a compound consisting of p-(benzyloxy)calix[6]arene or p-(benzyloxy)calix[7]arene comprising bringing rubidium hydroxide, at a total concentration greater than or equal to 0.3 equivalent and less than or equal to 0.5 equivalent, into contact with p-(benzyloxy)phenol and formaldehyde, as defined above, in which the mixture of solvents of the crystallization stage comprises DMSO and a polar solvent such as acetone.

The precipitate obtained corresponds to the purified mixture of p-(benzyloxy)calix[9-20]arenes.

X-axis: ln(M) where M represents the molecular weight of the p-(benzyloxy)calix[4-16]arenes.

Y-axis: ln(D) where D represents the self diffusion coefficient of the molecules which depends among other things on their hydrodynamic volume determined by diffusion NMR PGSE.

This curve makes it possible to link the self-diffusion coefficient to the average molar mass of the pure calixarenes.

Figure 1:
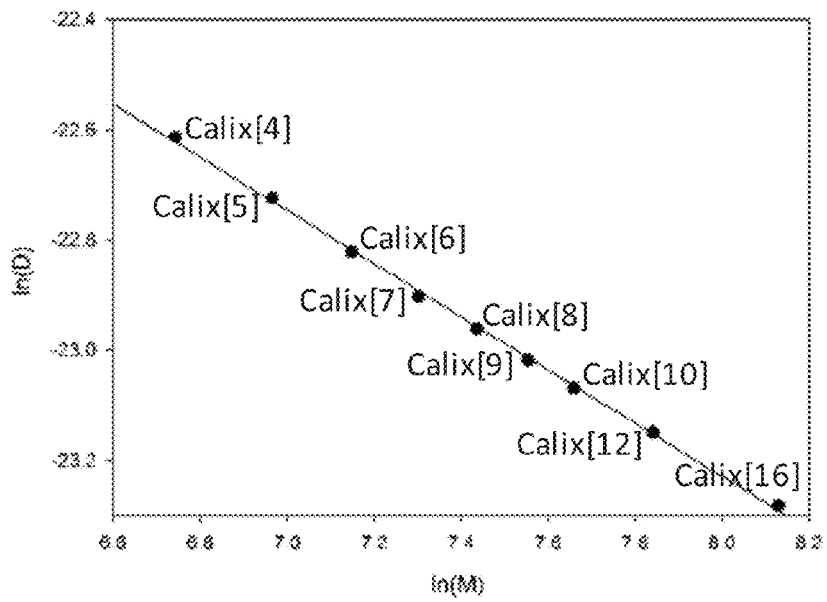
FIG. 1 shows the calibration curve obtained with pure samples of p-(benzyloxy)calix[4-16]arenes using PGSE (Pulse Gradient Spin Echo) diffusion NMR. It makes it possible to validate the molar mass of the pure p-(benzyloxy) calix[4-16]arenes determined by size exclusion chromatography.
Figure 2:
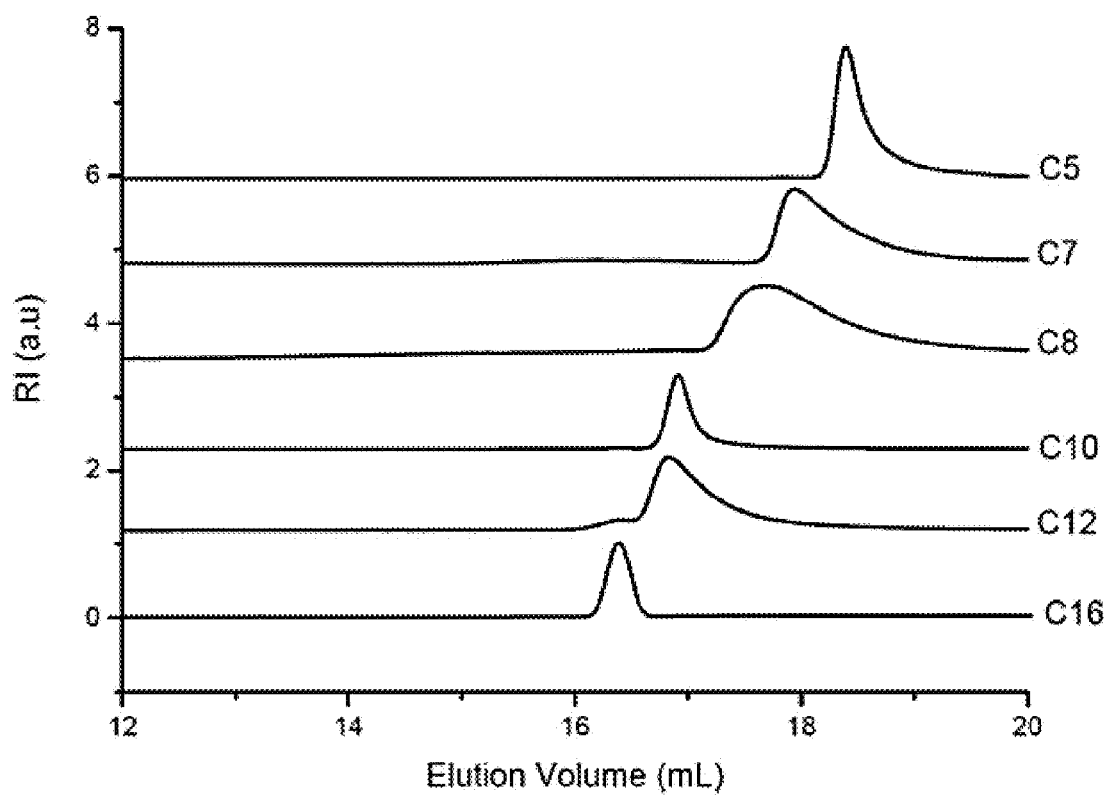

FIG. 2 shows the size exclusion chromatography of the pure samples of p-(benzyloxy)calix[5]arene, p-(benzyloxy) calix[7]arene, p-(benzyloxy)calix[8]arene, p-(benzyloxy) calix[10]arene, p-(benzyloxy)calix[12]arene and p-(benzyloxy)calix[16]arene.

This technique makes it possible to separate the molecules as a function of their hydrodynamic volume and to estimate the molar mass of pure samples or samples in a mixture starting from a range of pure standards. The molar mass representative of a pure calixarene or of a mixture of calixarenes is expressed as a "peak molar mass" (Mp) and average molar masses (Mz).

X-axis: Elution volume: Ve (ml)

Y-axis: RI signal (refraction index), corresponding to the refraction index of samples or of standards in solution leaving the chromatography column.

Figure 3:
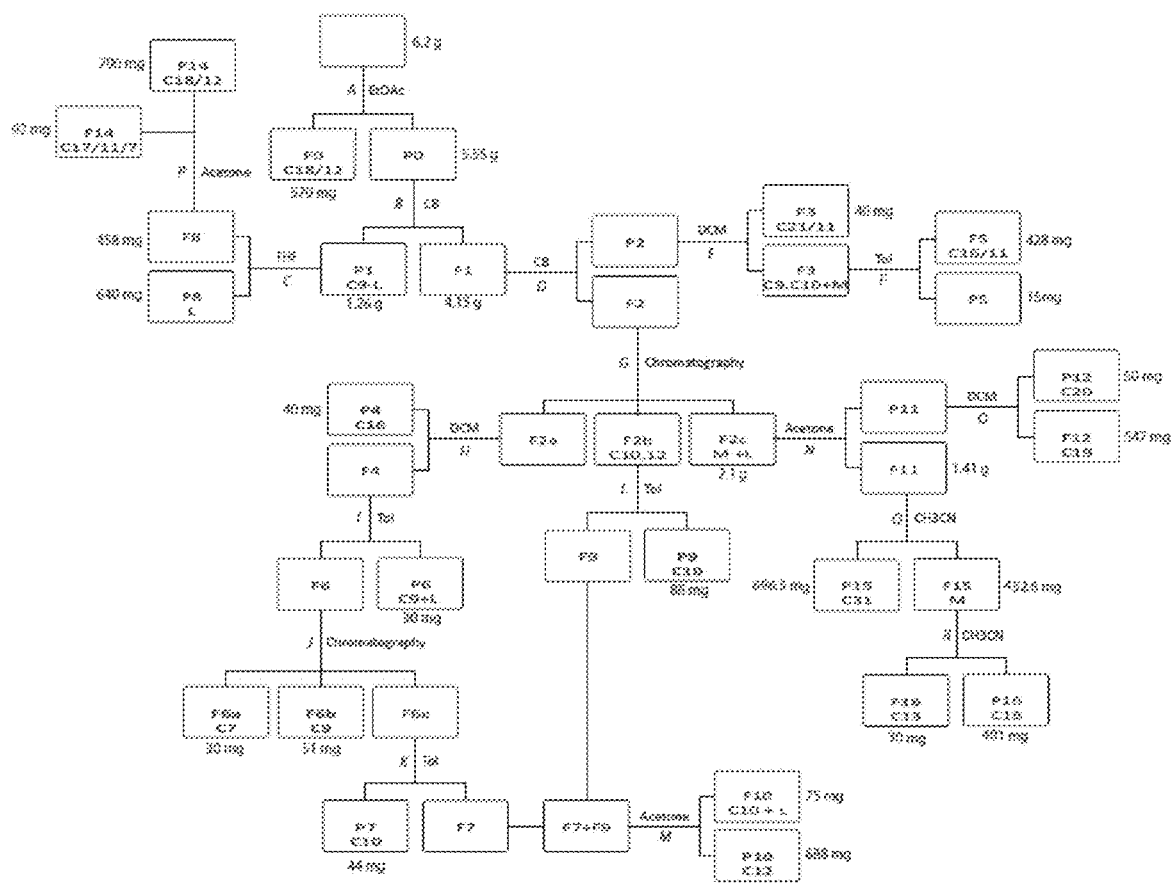

FIG. 3 shows a diagram for the purification of a mixture of large calixarenes obtained after the stage of crystallization from the acetone-DMSO mixture (10% by volume of DMSO). The abbreviations PX and FX correspond respectively to the precipitate of the fraction X and the filtrate of the fraction X. The fractions in bold type correspond to isolated pure calixarenes.

Each letter in italics corresponds to a purification stage, carried out in chronological order under the following conditions:

A: The crude product containing the mixture of calixarenes is stirred in ethyl acetate then filtered in order to obtain the Fractions P0 and F0.

B: The precipitate P0 is heated under reflux under argon and with stirring in 450 mL of chlorobenzene for 1 h then filtered in order to obtain the fractions P1 and F1.

C: The precipitate P1 is placed overnight under vigorous stirring in 40 mL of THF, filtered and copiously rinsed with THF in order to obtain the fractions P8 (640 mg, Mp corresponds to 20 units) and F8.

D: F1 is heated under reflux under argon and with stirring in 75 mL of chlorobenzene then cooled down and stirred at ambient temperature for 1 h. The solution is placed overnight at −20° C. and filtered in order to obtain the fractions P2 and F2.

E: P2 is placed overnight with stirring in 20 mL of dichloromethane at ambient temperature in order to obtain the fractions F3 and P3 (40 mg, mixture of calixarenes the Mps of which correspond to 22, 11 and 8 units).

F: F3 is dissolved in 40 mL of toluene under reflux then cooled to ambient temperature. After stirring for 4 h at ambient temperature, the suspension is filtered in order to obtain F5 (428 mg, mixture of calixarene the Mps of which correspond to 11 and 17 units) and P5 (15 mg).

G: F2 is dissolved hot in toluene and deposited on a silica column. The calixarene mixture is firstly eluted in dichloromethane in order to obtain the fractions F2a and F2b, then in tetrahydrofuran in order to obtain the fraction Fc.

H: 15 ml, of DCM is added to the fraction F2a and a white precipitate immediately appears. After leaving at rest for 1 h without stirring and the suspension is filtered in order to obtain P4 (40 mg, pure calix[16]arene) and F4.

I: F4 is heated briefly under reflux of toluene (20 mL) until total dissolution then placed at ambient temperature for 24 h without stirring. A suspension is obtained, which is filtered in order to obtain the fractions F6 and P6 (30 mg, mixture of large calixarenes).

J: F6 is dissolved in toluene then deposited on a silica column. The chromatography is carried out with an eluent gradient 70/30 to 100/0 of dichloromethane/toluene. The following are isolated, by order of elution: calix[7]arene (30 mg), calix[9]arene and a mixture of calix[10+12]arenes (fraction F6c).

K: F6c is heated briefly under reflux of toluene (6 mL) until total dissolution then placed at ambient temperature for 48 h without stirring. A suspension is obtained that is diluted in 20 mL of toluene. The suspension is filtered in order to obtain P7 (44 mg, pure calix[10]arene) and F7.

L: F2b is dissolved in 10 mL of toluene. A white precipitate rapidly appears and the suspension is stored for 5 days without stirring. 25 mL of toluene is added and, after 2 weeks without stirring, the suspension is filtered in order to obtain P9 (88 mg, pure calix[10]arene) and F9.

M: F7 and F9 are combined, dispersed in 150 mL of acetone then for 1 h under reflux of the solvent. The suspension is filtered in order to obtain P10 (688 mg, pure calix[12] arene) and F5 (75 mg, mixture of calix[10]arene and other large calixarenes).

N: F2c is placed under stirring in acetone at ambient temperature for 24 h then filtered in order to obtain a precipitate. This precipitate is subjected to three cycles of washings/filtrations in acetone. P11 is obtained (512 mg) and, after combining the filtrates, F11 (1.43 g).

O: P11 is placed under stirring in 25 mL of dichloromethane over a weekend at ambient temperature. P12 (50 mg, mixture of calixarenes of which Mp correspond to 21 units) and F12 (547 mg, two populations the Mps of which correspond to 19 and 30 units) are obtained.

P: F8 and P13 are combined and placed under stirring in acetone for 24 h in order to obtain P14 (790 mg, two populations, the Mps of which correspond to 19 and 12 units) and F14 (92 mg, two populations the Mps of which correspond to 17 and 11 units).

Q: F11 is mixed with 50 mL of acetonitrile. After heating for 15 min under reflux of the solvent, a type of viscous black oil deposits on the walls of the flask and the supernatant is immediately separated. This operation is repeated and P15 is obtained (696.5 mg, mixture of calixarenes the Mps of which correspond to 34 units) and, after combining the filtrates, F15 (425.6 mg).

R: F15 is placed under stirring in 50 mL of acetonitrile at ambient temperature for 24 h. F16 (30 mg, pure calix[13] arene) and P16 (401 mg, two populations the Mps of which correspond to 18 and 12 units) are obtained.

FIG. 4 shows all of the size exclusion chromatographies carried out on the mixtures of large calixarenes originating from the purification diagram shown in FIG. 3. Each chromatogram includes calix[16]arene as a reference.

FIG. 5 shows the Maldi-Tof mass spectra of the pure samples of p-(benzyloxy)calix[9]arene, p-(benzyloxy)calix[10]arene, p-(benzyloxy)calix[12]arene and p-(benzyloxy)calix[16]arene. This technique makes it possible to determine with precision the molar mass of a compound in order to arrive at its chemical composition.

FIG. 6 shows the NMR spectra of the pure samples of p-(benzyloxy)calix[9]arene, p-(benzyloxy)calix[10]arene, p-(benzyloxy)calix[12]arene, p-(benzyloxy)calix[13]arene and p-(benzyloxy)calix[16]arene.

Figure 7:
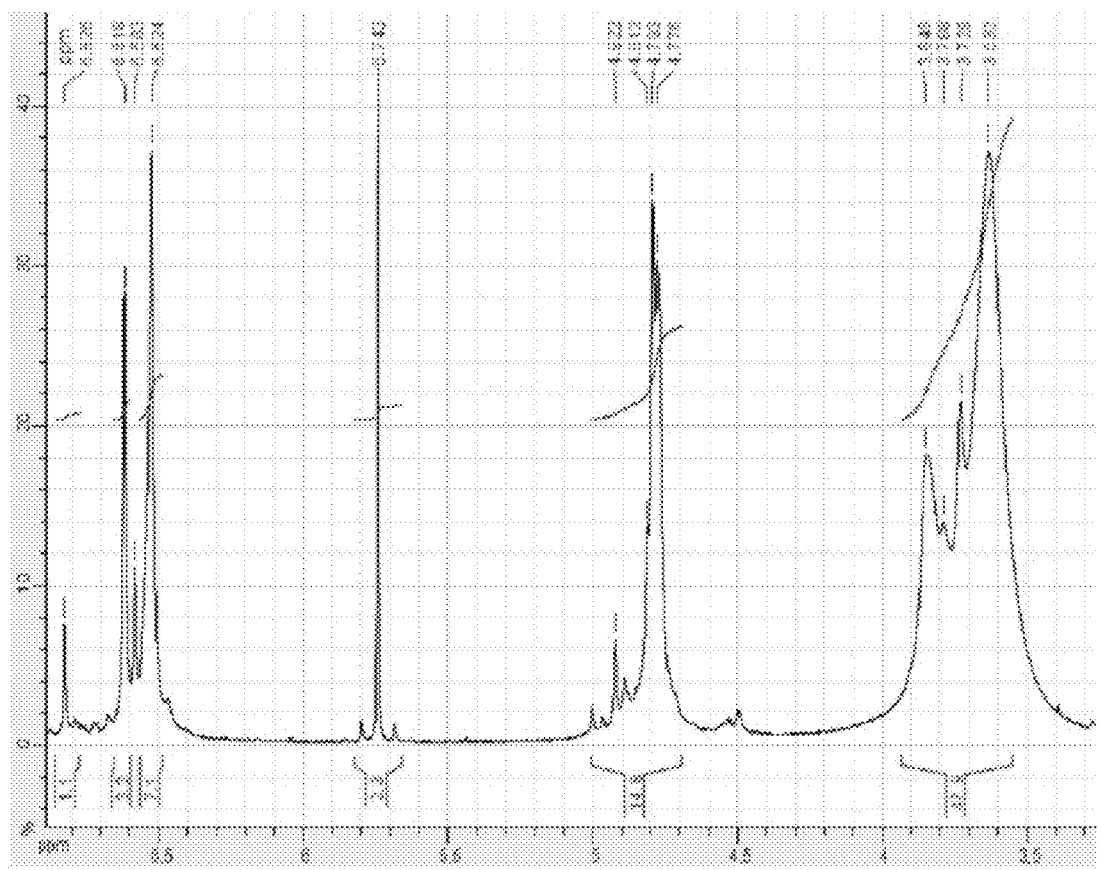

FIG. 7 shows an NMR analysis of the crude reaction product with respect to Example 2.

FIG. 8.1 shows an NMR analysis of the crude reaction product with respect to Example 3.

FIG. 8.2 shows an NMR analysis of the purified sodium monosalt with respect to Example 3.

Figure 9:
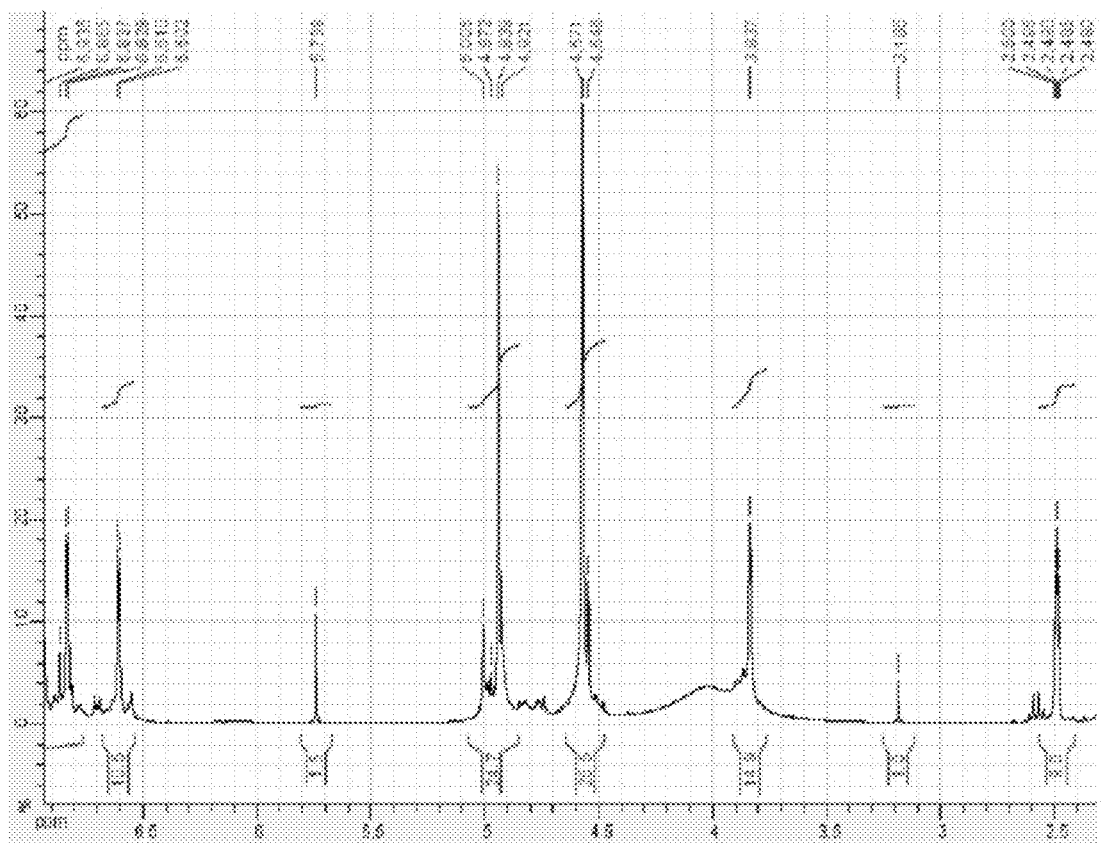

FIG. 9 shows an NMR analysis of the crude reaction product with respect to Example 3.1.

Figure 10:
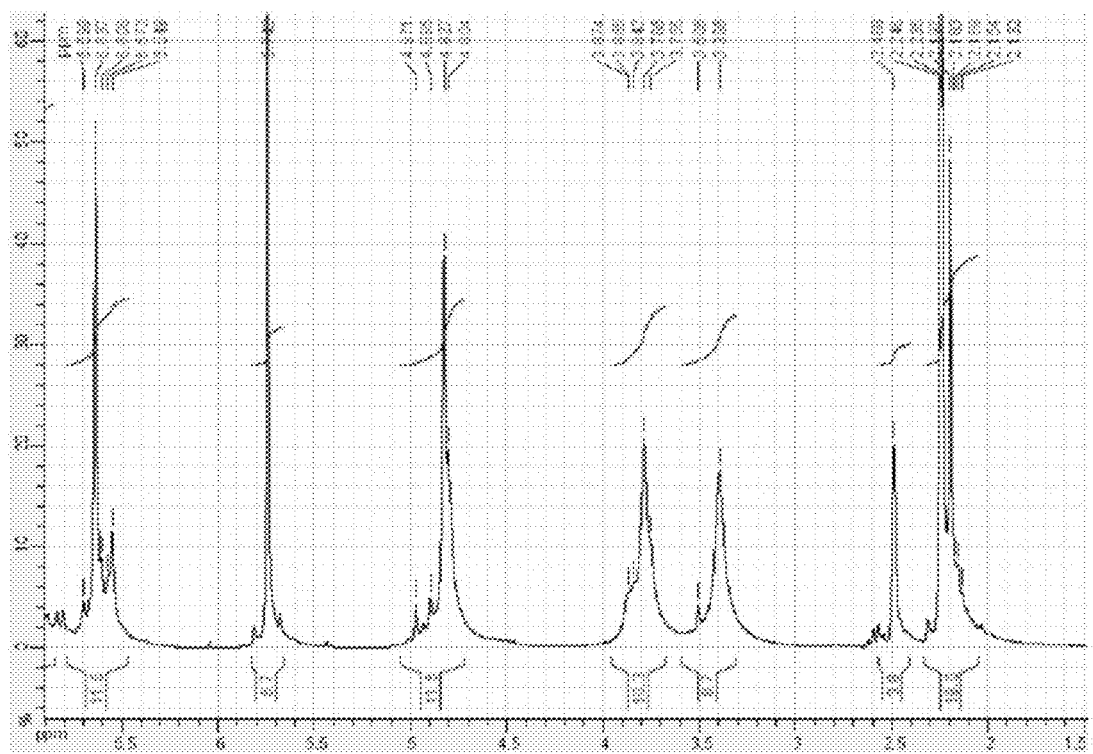

FIG. 10 shows an NMR analysis of the crude reaction product with respect to Example A.1.

Figure 11:
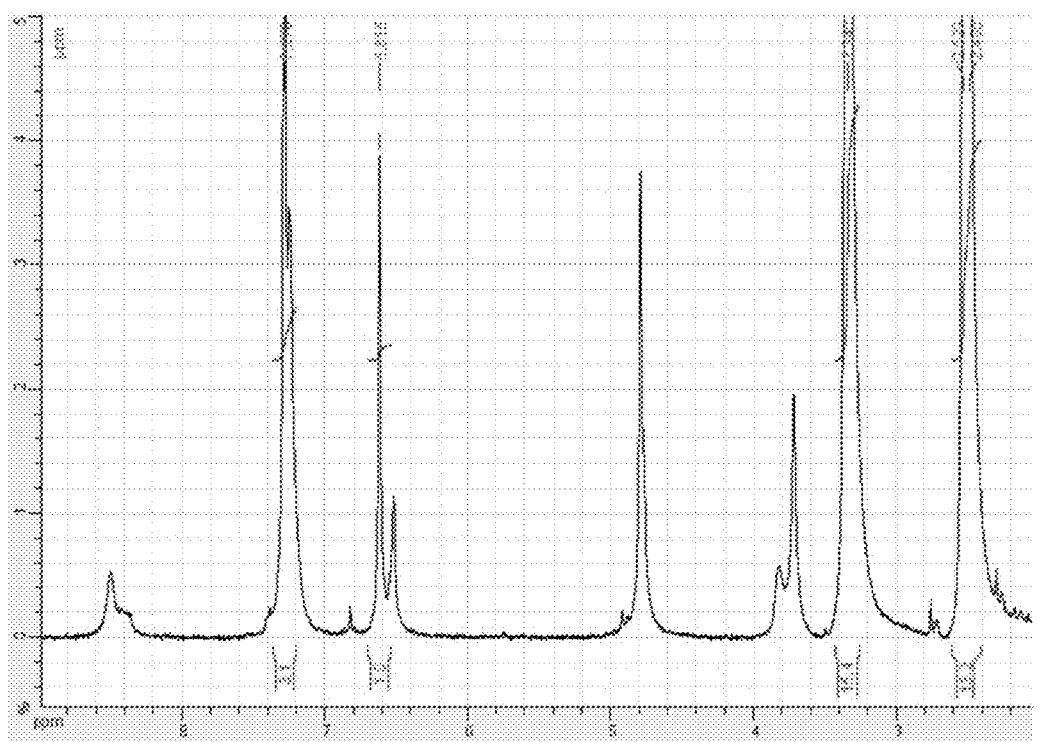

FIG. 11 shows an NMR analysis of the bright orange solution described in Example A.2.

Figure 12:
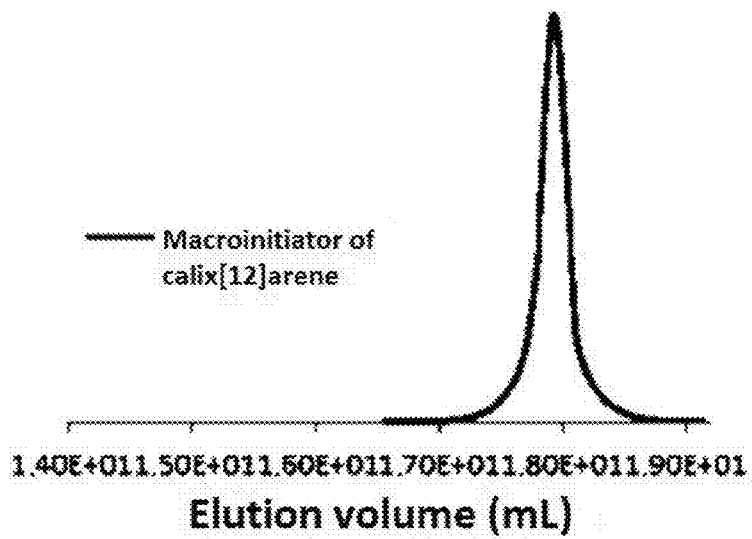

FIG. 12 shows the chromatogram (SEC) of the macroinitiator obtained from calix[12]arene (Example C).

Figure 13:
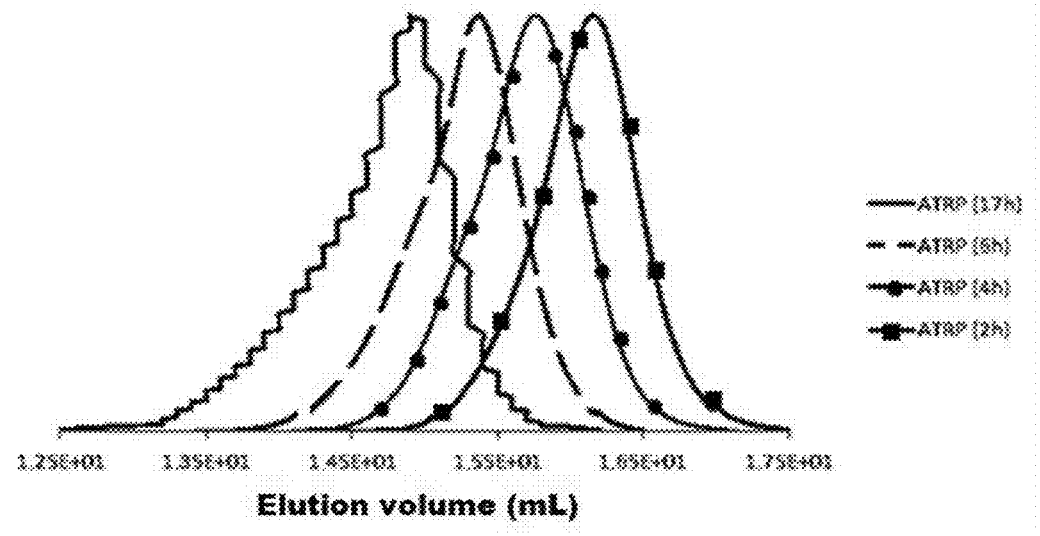
Figure 14:
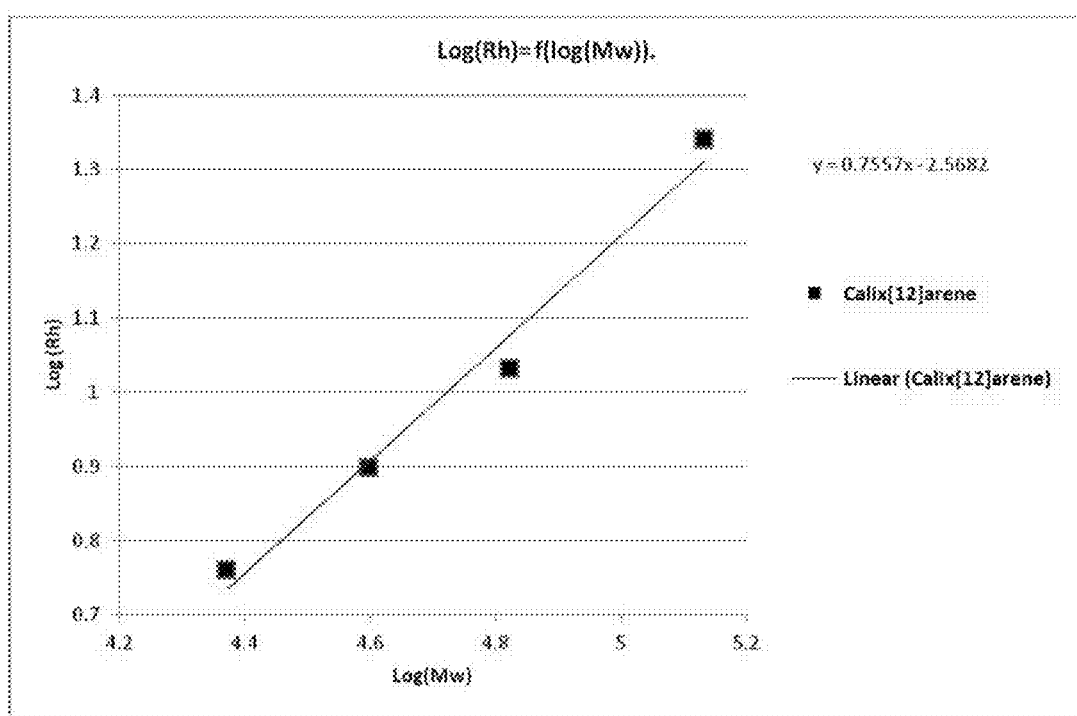

FIG. 13 shows the chromatogram (SEC) of the star polymers obtained from calix[12]arene, said polymers differing by the duration of the ATRP process FIG. 14 shows the characterization of the structures of the star polymers, by expressing log Rh where Rh corresponds to the hydrodynamic radius of the polymer studied, as a function of log Mw where Mw is the molar mass of the polymer.

EXAMPLES

Example 1

Preparation and Purification of a Mixture of p-(Benzyloxy)Calix[9-20]Arenes with RbOH (0.6 eq)

In a 2-liter flask equipped with a magnetic stirrer and a Dean-Stark, a suspension of 50 g of 4-(benzyloxy)phenol (0.25 equivalent), 15 g of paraformaldehyde (0.5 equivalent) in 670 ml of xylene (mixture of isomers) is prepared.

This suspension is heated. At 90° C., 18 ml (0.6 equivalent with respect to the phenol) of a solution of RbOH at 50% by weight in water is rapidly added.

The solution is heated under reflux for 6 h and left to return to ambient temperature.

A proton NMR analysis shows that the reaction medium is 60% constituted by large calixarenes, and contains a proportion of 15% of p-(benzyloxy)calix[5]arene.

The different constituents of this mixture can then be purified according to the sequence described in FIG. 3.

Example 2

Preparation of a Mixture of p-(Benzyloxy)Calix[9-20]Arenes with CsOH (0.6 Equivalent with Respect to Phenol)

In a 2-liter flask equipped with a magnetic stirrer and a Dean-Stark, a suspension of 50 g of 4-(benzyloxy)phenol (0.25 equivalent) and 15 g of paraformaldehyde (0.5 equivalent) in 670 ml of xylene (mixture of isomers) is prepared.

This suspension is heated. At 90° C., 27 ml (0.6 equivalent with respect to the phenol) of a 50% CsOH solution by weight in water is rapidly added.

The solution is taken to reflux for 6 h and left to return to ambient temperature.

An NMR analysis (FIG. 7) of the crude reaction product shows that it is 60% constituted by large calixarenes.

The suspension is neutralized with 500 ml of THF containing 30 ml of a 37% HCl solution under vigorous stirring.

The resulting fluid suspension is filtered, and the filtrate evaporated to dryness. The solid obtained is washed with 500 ml of acetonitrile and filtered (in order to remove the most polar or most soluble species, such as linear oligomer radicals, calix[5]arenes and homooxacalixarene).

After filtration and drying with a vacuum pump, 32 g of a brown solid is recovered, which is dissolved hot in a mixture of 75 ml of DMSO and 750 ml of acetone.

The resulting dark orange clear solution is left in a refrigerator for two days, during which period a microcrystalline precipitate (20 g) forms.

An NMR study shows that this precipitate is constituted exclusively by large calixarenes.

Example 3

Preparation of a Mixture of
p-(Benzyloxy)Calix[9-20]Arenes and
p-Benzyloxycalix[7]Arene in the Form of the
Sodium or Potassium Salt with Sodium Hydroxide
or Potassium Hydroxide (0.6 eq)

In a 2-liter flask equipped with a magnetic stirrer and a Dean-Stark, a suspension of 50 g of 4-(benzyloxy)phenol (0.25 equivalent) and 15 g of paraformaldehyde (0.5 equivalent) in 670 ml of xylene (mixture of isomers) is prepared.

This suspension is heated. At 90° C., 6.5 g of NaOH in 10 ml of water (0.6 equivalent with respect to the phenol) is rapidly added. The solution is heated under reflux for 8 h and left to return to ambient temperature.

An NMR analysis (FIG. 8.1) of the crude reaction product shows that it is constituted by a mixture of p-(benzyloxy)calix[7] and [8]arenes as well as unreacted dimer, accompanied by a much smaller proportion of large calixarenes.

Filtration of this product leads to the obtention of p-(benzyloxy)calix[7]arene in the form of the sodium monosalt (FIG. 8.2).

Example 3.1

Obtention of the Dimer

In a 2-liter flask equipped with a magnetic stirrer and a Dean-Stark, is prepared a suspension of 50 g of 4-(benzyloxy) phenol (0.25 equivalent) and 15 g of paraformaldehyde (0.5 equivalent) in 670 ml of xylene (mixture of isomers).

This suspension is heated. At 90° C., 6.5 g of NaOH in 10 ml of water (0.6 equivalent with respect to the phenol) is rapidly added. The solution is heated under reflux for 1 h and left to return to ambient temperature.

An NMR analysis (FIG. 9) of the crude reaction product shows that it is constituted almost exclusively by the dimer:

This product is recovered by simple filtration. Yield: 80%.

Example 4

Preparation of a Mixture of
p-(Methoxy)Calix[9-20]Arenes with CsOH (0.6 eq)

In a 2-liter flask equipped with a magnetic stirrer and a Dean-Stark, a suspension of 31 g of 4-(methoxy)phenol (0.25 equivalent), 15 g of paraformaldehyde (0.5 equivalent) in 670 ml of xylene (mixture of isomers) is prepared.

This suspension is heated. At 90° C., 15 ml (0.6 equivalent with respect to the phenol) of a CsOH solution at 50% by weight in water is rapidly added.

The solution is taken to reflux for 6 h and left to return to ambient temperature.

A proton NMR analysis shows that the reaction medium is 50% constituted by large calixarenes.

Example 4

Preparation of a Mixture of
p-(Octyloxy)Calix[9-20]Arenes with CsOH (0.6 eq)

In a 2-liter flask equipped with a magnetic stirrer and a Dean-Stark, a suspension of 56 g of 4-(octyloxy)phenol (0.25 equivalent), 15 g of paraformaldehyde (0.5 equivalent) in 670 ml of xylene (mixture of isomers) is prepared.

This suspension is heated. At 90° C., 26.5 ml (0.6 equivalent with respect to the phenol) of a CsOH solution at 50% by weight in water is rapidly added.

The solution is taken to reflux for 6 h and left to return to ambient temperature.

A proton NMR analysis shows that the reaction medium is 70% constituted by large calixarenes.

Example 6

Use of Large Calixarenes for the Synthesis of
Nanomaterials: Star Polymers

The procedure used is in two stages. During the first stage, the phenol groups of the calixarene are acylated with bromopropionyl bromide. These groups constitute polymerization initiators, used during a second stage for growing polystyrene chains.

Synthesis of the initiator for calix[12]arene.

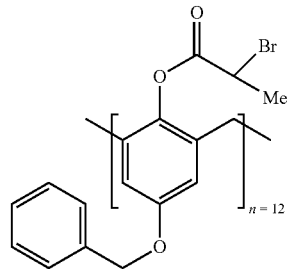

The large calixarene is introduced into a Schlenk tube (500 mg, 0.0002 mol). Then 5 mL of DMF and 1.5 mL of Et$_3$N are added under argon. The system is immersed in an ice bath. Then 300 µL of bromopropionyl bromide is introduced. The solution is stirred for 1 h. A precipitation is carried out from 50 mL of MeOH followed by filtration under vacuum. The initiator is solubilized in a few milliters of THF. Then a second precipitation is carried out with 50 mL of MeOH followed by filtration under vacuum. The product is dried in a desiccator.

Yield=60%.

1H NMR (350 MHz, CDCl$_3$) $\delta_{ppm}$: 7.1-7.6 (m, 60H, —OCH$_2$—Ar), 6.8-6.4 (m, 24H, Ar), 5.1-4.7 (m, 24H, —OCH$_2$—Ar—), 4-3.5 (m, 24H, —Ar(phenol)-CH$_2$—), 3-1.5 (m, 24H, CH$_3$—CH(COR)—Br), 2-1.5 (m, 36H, CH$_3$—CH(COR)—Br).

This macroinitiator is also characterized by size exclusion chromatography (FIG. 12).

Synthesis of the Star Polymer by Atom Transfer Radical Polymerization (ATRP)

CuBr (25 mg, 0.00017 mol), bipyridine (80 mg, 0.00052 mol), the initiator synthesized previously (60 mg, 0.00017 mol) and 2 mL of styrene are introduced into a Schlenk tube under argon. The reaction medium is degassed using 3 freeze-thaw cycles. The Schlenk tube is immersed in an oil bath heated at 100° C. for a given period of time. The mixture is solubilized in THF. The mixture is filtered on a column of basic $Al_2O_3$. The polymer is precipitated from MeOH $$\left(\text{with a ratio} = \frac{THF}{MeOH} = 10\right),$$

then filtered under vacuum and rinsed with MeOH. The product is dried in a desiccator.

Yield=50%.

1H NMR (360 MHz, $CDCl_3$) $\delta_{ppm}$: 7.1-7.6 (m, 5H, —$OCH_2$—Ar), 7.2-6.9 (m, 5H, $Ar_{styrene}$), 7.2-6.9 (m, 1H, —$CH_2$—CH(Ar)—$CH_2$—), 6.8-6.4 (m, 2H, Ar), 2.1-1.6 (m, 2H, —CH—$CH_2$—CH—), 2.1-1.6 (m, 1H, $HO_2C$—CH($CH_3$)—$CH_2$—), 1.6-1.3 (m, 3H, $CH_3$—CH—).

The star polymers obtained, which differ by the duration of the ATRP, are also characterized by size exclusion chromatography (FIG. 13).

Study of the Structure of the Polymers in Solution.

In order to study the behaviour of said star polymers in solution a scaling law can be used:

$Rh=KM^\alpha$ where Rh corresponds to the hydrodynamic radius, M correspond to the molar mass; K and $\alpha$ are coefficients. The terms K and $\alpha$ are coefficients with the polymer.

$\log Rh = \log K + \alpha \log M$

The term $\alpha$ provides information on the behaviour of the polymers in solution:

If $\alpha$ tends to 1 then the polymer behaves as a linear polymer.

If $\alpha$ tends to 0.5 then the polymer behaves as a random coil.

If $\alpha$ tends to 0 then the polymer behaves as a hard sphere.

The curve of the hydrodynamic radius (measured by light scattering) as a function of the molar mass (obtained by measuring the molar mass of the polystyrene branches (after "uncoupling" of the central calixarene core by saponification) therefore makes it possible to provide information on the structure of these nanoobjects in solution (FIG. 14).

In the case of the star polymers derived from calix[12] arene, the behaviour is that of a linear oligomer, they therefore form well-defined nanoobjects in solution (THF), which are potentially useful for encapsulation and vectorization.

Comparative Examples

Use of a Base in a Proportion Less than or Equal to 0.5 eq with p-Benzyloxyphenol Example A Obtaining a Compound Consisting of p-(Benzyloxy) Calix[6]Arene or p-(Benzyloxy)Calix[7]Arene, in the Form of the Caesium Salt or Neutralized, or of a Mixture Comprising p-(Benzyloxy)Calix[6]Arene and p-(Benzyloxy)Calix[7]Arene with Caesium Hydroxide Example A.1

Caesium Hydroxide Concentration of 0.15 equivalent

A suspension of 50.6 g of p-(benzyloxy)phenol (0.254 mol), 20 g (0.667 mol) of paraformaldehyde (melting point: 135° C.) in 700 ml of xylene is placed under argon in a 2-liter three-necked flask equipped with a mechanical stirrer and a "Dean-Stark"-type water trap.

The suspension is heated under stirring. When the temperature reaches 90° C. 7.4 ml (0.0425 mol) of a CsOH solution at 50% (by weight) in water, is rapidly added using a syringe (and under argon flushing).

The suspension is left under reflux for 6 h, a period of time during which the formation of a voluminous white precipitate is observed.

An analysis of this crude reaction product (FIG. 10) shows that it is constituted mainly by the p-(benzyloxy)calix[7] arene caesium salt.

This precipitate is filtered, washed with xylene, then with pentane. m=35 g, yield of p-(benzyloxy)calix[7]arene (in the form of the caesium monosalt): 58%.

The spectroscopic characteristics of this precipitate correspond to those of a p-(benzyloxy)calix[7]arene monoanion.

1H NMR (DMSO-$d_6$): (chemical shifts, ppm) 7.60-7.20 (multiplet, aromatics); 6.72 (fine singlet, hydroquinone); 4.93 (fine singlet, benzyl); 3.71 (fine singlet, intracyclic methylenes).

Mass spectrometry (MALDI, DHB matrix): m/z=1617.41 $(M+Cs)^+$.

A 1 g sample of this precipitate is suspended in 5 ml of dichloromethane, then neutralized with an aqueous solution of concentrated HCl, under vigorous stirring for 24 h.

The organic phase is recovered, then evaporated to dryness with a Rotavapor.

0.91 g of a white solid is recovered, the spectroscopic characteristics of which are perfectly consistent with neutral p-(benzyloxy)calix[7]arene.

1H NMR (DMSO-$d_6$): (chemical shifts, ppm) 7.30 (broad multiplet, aromatics); 6.62 (fine singlet, hydroquinone); 4.84 (fine singlet, benzyl); 3.74 (fine singlet, intracyclic methylenes).

Mass spectrometry (MALDI, DHB matrix): m/z=1507.65 $(M+Na)^+$.

The observed loss of mass (90 mg) is completely consistent with that expected for the neutralization of a caesium monosalt: p-(benzyloxy)calix[7]arene)-$Cs^+$→p-(benzyloxy)calix [7]arene.

Example A.2

Concentration of Caesium Hydroxide of 0.3 Equivalent

A suspension of 50.6 g of p-(benzyloxy)phenol (0.254 mol), 20 g (0.667 mol) of paraformaldehyde (melting point: 135° C.) in 700 ml of xylene is placed under argon in a three-necked 2-liter flask equipped with a mechanical stirrer and a "Dean-Stark"-type trap.

The suspension is heated under stirring. When the temperature reaches 90° C., 14.8 ml (0.085 mol) of a CsOH solution at 50% (by weight) in water is rapidly added using a syringe (and under argon flushing).

The suspension is left under reflux for 5 hours 30 minutes. Then, a perfectly clear, bright orange solution is obtained.

An NMR analysis (FIG. 11) of this solution shows that it comprises mainly p-(benzyloxy)calix[6]arene, accompanied by a low percentage of large calixarenes.

Then 100 ml a 37% HCl solution in water is added, and the formation of a precipitate is observed. The suspension is left under vigorous stirring for two days, then evaporated to dryness in a rotary evaporator.

After washing with 500 ml of water (removal of the salts and excess HCl), the solid is dissolved hot (130° C.) in 200 ml of DMSO. A clear black solution is then obtained, to which 2 l of acetone is added hot.

After returning to ambient temperature, this clear solution is left for a week, during which a crystalline precipitate of p-(benzyloxy)calix[6]arene (18 g) deposits on the walls of the flask.

The filtrate is evaporated in a rotavapor, then with a heat gun until a black solid is obtained. This solid is washed with acetone, which leads to the recovery of a second batch of p-(benzyloxy)calix[6]arene (10 g). Total: 28 g, yield 51%.

1H NMR (DMSO-$d_6$): (chemical shifts, ppm) 7.30 (broad multiplet, aromatics); 6.62 (fine singlet, hydroquinone); 4.79 (fine singlet, benzyl); 3.72 (fine singlet, intracyclic methylenes).

Mass spectrometry (MALDI, DHB matrix): m/z=1295.49 $(M+Na)^+$.

Example B

Obtaining a Compound Consisting of p-(Benzyloxy)Calix[6]Arene or p-(Benzyloxy)Calix[7]Arene in the Neutralized Form or p-(Benzyloxy)Calix[8]Arene or a Mixture Comprising p-(Benzyloxy)Calix[6]Arene, p-(Benzyloxy)Calix[7]Arene and p-(Benzyloxy)Calix[8]Arene with Sodium or Potassium Hydroxide

Example B.1

Sodium or Potassium Hydroxide Concentration of 0.15 Equivalent

A suspension of 34.5 g of p-(benzyloxy)phenol (0.173 mol), 20 g (0.667 mol) of paraformaldehyde (melting point: 135° C.) in 450 ml of xylene is placed under argon in a 1-liter three-necked flask equipped with a mechanical stirrer and a "Dean-Stark"-type trap.

The suspension is heated under stirring. When the temperature reaches 95° C., a solution of 1.43 g (0.03 mol) of KOH in 6 ml of Millipore water is rapidly added using a syringe (and under argon flushing). The immediate appearance of a yellow coloration is observed.

The reaction medium is taken to reflux for 3 hours 30 minutes, a period during which the formation of copious white precipitate and a bright orange solution is observed.

After returning to ambient temperature, the precipitate is recovered by filtration, washed with 100 ml of xylene and 300 ml of pentane.

The analyse of this precipitate indicates that it is constituted by pure p-(benzyloxy)calix[7]arene. M=20 g, yield 54%.

Characterizations:

1H NMR (DMSO-$d_6$): (chemical shifts, ppm) 7.30 (broad multiplet, aromatics); 6.62 (fine singlet, hydroquinone); 4.84 (fine singlet, benzyl); 3.74 (fine singlet, intracyclic methylenes). Mass spectrometry (MALDI, DHB matrix): m/z=1524.62 $(M+K)^+$.

Example B.2

Sodium or Potassium Hydroxide Concentration of 0.3 Equivalent

A suspension of 51.5 g of p-(benzyloxy)phenol (0.258 mol), 20 g (0.667 mol) of paraformaldehyde (melting point: 135° C.) in 700 ml of xylene is placed under argon in a three-necked 2-liter flask equipped with a mechanical stirrer and a "Dean-Stark"-type trap.

The suspension is heated under stirring. When the temperature reaches 90° C., 3.056 g of NaOH (0.0764 mol) in 10 ml of water is rapidly added using a syringe (and under argon flushing).

The suspension is left under reflux for 4 hours 30 minutes, a period of time at the end of which the reaction medium solidifies.

After returning to ambient temperature, the reaction medium is neutralized with 500 ml of a 2M HCl solution, under very vigorous stirring.

The resulting emulsion is evaporated to dryness and washed with 500 ml of water (removal of the sodium salts).

The resulting orange-coloured solid is washed with 500 ml of THF and the resulting white precipitate is filtered, which leads to the recovery of 20 g of pure p-(benzyloxy)calix[8] arene. Yield: 36.6%.

1H NMR (DMSO-$d_6$): (chemical shifts, ppm) 7.30 (broad multiplet, aromatics); 6.58 (fine singlet, hydroquinone); 4.80 (fine singlet, benzyl); 3.77 (fine singlet, intracyclic methylenes).

Mass spectrometry (MALDI, DHB matrix): m/z=1719.62 $(M+Na)^+$.

The corresponding filtrate is evaporated to dryness and dissolved hot in 45 ml of DMSO, which leads to the formation of a black homogeneous solution. 1 l of toluene is added thereto, and the clear dark orange solution is placed in a freezer (−23° C.) for 1 week, which leads to the formation of a microcrystalline precipitate. This precipitate is filtered, and its $^1$H NMR analysis shows that it is pure p-(benzyloxy)calix [6]arene; m=6.3 g, 11%.

1H NMR (DMSO-$d_6$): (chemical shifts, ppm) 7.30 (broad multiplet, aromatics); 6.62 (fine singlet, hydroquinone); 4.79 (fine singlet, benzyl); 3.72 (fine singlet, intracyclic methylenes).

Mass spectrometry (MALDI, DHB matrix): m/z=1295.49 $(M+Na)^+$.

The corresponding DMSO/toluene filtrate is evaporated until an orange liquid is obtained. After the addition of 1 l of methanol and filtration, 28.5 g of pure p-(benzyloxy)calix[7] arene is recovered. Yield: 52%.

1H NMR (DMSO D6): (chemical shifts, ppm) 7.30 (broad multiplet, aromatics); 6.62 (fine singlet, hydroquinone); 4.84 (fine singlet, benzyl); 3.74 (fine singlet, intracyclic methylenes).

Mass spectrometry (MALDI, DHB matrix): m/z=1524.62 (M+K)$^+$.

The invention claimed is:

1. A process for the preparation of a p-(R-oxy)calixarene or a mixture of at least two of said p-(R-oxy)calixarenes, comprising:

mixing (i) at least one base, (ii) at least one phenol substituted in position 4 of following formula (I):

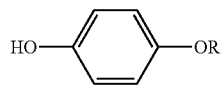

(I)

in which R is selected from:

a benzyl group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aORb$, $R_a$ and $R_b$ representing independently of one another a linear or branched $C_1$-$C_{20}$ alkyl, a linear or branched $C_1$-$C_{20}$ alkyl group, a linear or branched PEG-1 to 10, the —OH end group of which is alkylated with a linear or branched $C_1$-$C_{20}$ alkyl, (ii) a source of formaldehyde and (iii) an organic solvent, the mixture of said base, said phenol, said source of formaldehyde and said organic solvent constituting a reaction medium, heating said reaction medium to carry out a reaction, wherein said base being at a total concentration from more than 0.5 equivalent to 1.5 equivalent, with respect to said at least one phenol substituted in position 4 of formula (I), and wherein said reaction forms a p-(R-oxy)calixarene selected from the group consisting of a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, a p-(R-oxy)calix[20]arene, and a mixture of at least two of said p-(R-oxy)calixarenes in which said at least two p-(R-oxy)calixarenes are present in said mixture each at a level of at least 5 mol. %.

2. A process for preparing a p-(R-oxy)calixarene selected from the group consisting of a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, and a p-(R-oxy)calix[20] arene, or a mixture of at least two of said p-(R-oxy)calixarenes in which said at least two p-(R-oxy)calixarenes are present in said mixture each at a level of at least 5 mol. %, comprising a step of bringing a base, into contact with at least one phenol substituted in position 4 of following formula (I):

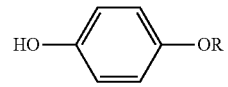

(I)

in which R is selected from:

a benzyl group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aORb$, $R_a$ and $R_b$ representing independently of one another a linear or branched $C_1$-$C_{20}$ alkyl, a linear or branched $C_1$-$C_{20}$ alkyl group, a linear or branched PEG-1 to 10, the —OH end group of which is alkylated with a linear or branched $C_1$-$C_{20}$ alkyl, a source of formaldehyde and an organic solvent, the mixture of said base, said phenol, said source of formaldehyde and said organic solvent constituting a reaction medium, said reaction medium being heated and said base being at a total concentration comprised from more than 0.5 equivalent to 1.5 equivalent with respect to said at least one phenol substituted in position 4 of formula (I).

3. The process according to claim 2, wherein said phenol substituted in position of formula (I) is selected from 4-benzyloxyphenol or 4-octyloxyphenol.

4. The process according to claim 2, wherein the source of formaldehyde is paraformaldehyde and the organic solvent is xylene.

5. The process according to claim 2, wherein said base is selected from caesium hydroxide and rubidium hydroxide.

6. The process according to claim 2, according to claim 5, comprising the following steps:

a. bringing caesium and/or rubidium hydroxide, into contact with at least one phenol substituted in position 4 of formula (I), said base being at a total concentration comprised from more than 0.5 equivalent to 1.5 equivalent, with respect to said at least one phenol substituted in position 4 of formula (I), a source of formaldehyde, in an organic solvent then heating while optionally removing said water formed from the reaction medium, in order to obtain:

a p-(R-oxy)calixarene selected from the group consisting of a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, and a p-(R-oxy)calix[20]arene, or, a mixture of at least two of said p-(R-oxy)calix[9-20] arenes in which said at least two p-(R-oxy)calixarenes are present in said mixture each at a level of at least 5 mol. %, in the salified form in the final reaction medium, b. neutralizing said salified form of said p-(R-oxy)calixarene or of said mixture in order to obtain said p-(R-oxy)calixarene or said mixture in the neutralized form.

7. The process according to claim 2, in which said base is selected from sodium hydroxide or potassium hydroxide in an aqueous solution.

8. The process according to claim 7, comprising the following steps:
   a. bringing sodium hydroxide or potassium hydroxide in an aqueous solution, into contact with at least one phenol substituted in position 4 of formula (I), said base being at a total concentration comprised from more than 0.5 equivalent to 1.5 equivalent with respect to said at least one phenol substituted in position 4 of formula (I), of the paraformaldehyde in an organic solvent then heating, in order to obtain:
      a p-(R-oxy)calixarene selected from the group consisting of a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, and a p-(R-oxy)calix[20]arene, or,
      a mixture of at least two of said p-(R-oxy)calixarenes in which said at least two p-(R-oxy)calixarenes are present in said mixture each at a level of at least 5 mol. %,
      and a p-(R-oxy)calix[7]arene,
      in the salified form in the final reaction medium,
   b. optionally filtering the reaction medium in order to obtain said p-(R-oxy)calix[7]arene in the form of the sodium or potassium monosalt, followed by an additional stage of neutralization of the p-(R-oxy)calix[7]arene in the form of the sodium or potassium monosalt in order to obtain the p-(R-oxy)calix[7]arene in the neutralized form and a filtered final reaction medium,
   c. neutralizing said final reaction medium or of said filtered final reaction medium in order to obtain:
      said p-(R-oxy)calixarene or said mixture, substantially devoid of p-(R-oxy)calix[7]arene, in the neutralized form, or
      said p-(R-oxy)calixarene or said mixture, in combination with p-(R-oxy)calix[7]arene, in the neutralized form,
   d. optionally purifying:
      of said p-(R-oxy)calixarene or of said mixture, substantially devoid of p-(R-oxy)calix[7]arene, in the neutralized form, or
      said p-(R-oxy)calixarene or said mixture, in combination with p-(R-oxy)calix[7]arene, in the neutralized form.

9. A phenolic dimer substituted in position 4 of following formula (II):

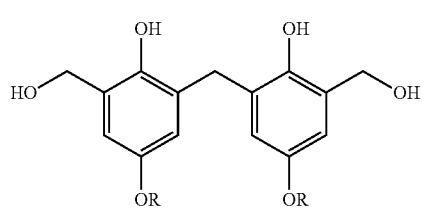

(II)

in which R is as defined in claim 1.

10. A p-(R-oxy)calix[n]arene or mixture of at least two p-(R-oxy)calix[n]arenes in which said at least two p-(R-oxy)calixarenes are present in said mixture each at a level of at least 5 mol. %, of following formula (III):

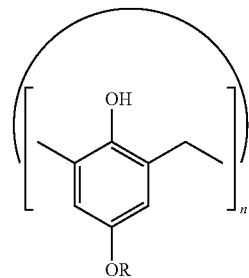

(III)

in which n is an integer comprised from 9 to 20, R being as defined in claim 1.

11. A method for the constitution of a material, comprising adding to said material a p-(R-oxy)calixarene selected from the group consisting of a p-(R-oxy)calix[9]arene, a p-(R-oxy)calix[10]arene, a p-(R-oxy)calix[11]arene, a p-(R-oxy)calix[12]arene, a p-(R-oxy)calix[13]arene, a p-(R-oxy)calix[14]arene, a p-(R-oxy)calix[15]arene, a p-(R-oxy)calix[16]arene, a p-(R-oxy)calix[17]arene, a p-(R-oxy)calix[18]arene, a p-(R-oxy)calix[19]arene, and a p-(R-oxy)calix[20]arene, or of a mixture of at least two of said p-(R-oxy)calix[9-20]arenes in which said at least two p-(R-oxy)calixarenes are present in said mixture each at a level of at least 5 mol. %, said material being able to be used in the implementation of a process for obtaining gels or foams, for the constitution of a material in the context of the mechanical reinforcement of materials, for the synthesis of metallic particles with controlled dimensions and a low dispersion, for nanofiltration, for gas filtration, for the complexing of ions, and for the vectorization or encapsulation of molecules.

12. A method for the constitution of a material, comprising adding to said material a p-(R-oxy)calix[n]arene or mixture of at least two p-(R-oxy)calix[n]arenes in which said at least two p-(R-oxy)calixarenes are present in said mixture each at a level of at least 5 mol. %, of following formula (III):

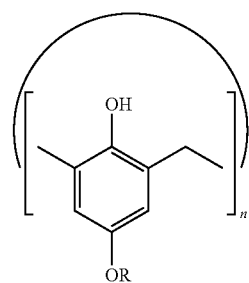

(III)

in which n is an integer comprised from 9 to 20, R being as defined in claim 1,
and:
said material being able to be used in the implementation of a process for obtaining gels or foams, for the constitution of a material in the context of the mechanical reinforcement of materials, for the synthesis of metallic particles with controlled dimensions and a low dispersion, for nanofiltration, for gas filtration, for the complexing of ions, and for the vectorization or encapsulation of molecules.

13. The process according to claim 1, wherein said at least one base is selected from the group consisting of potassium hydroxide, sodium hydroxide, lithium hydroxide, rubidium hydroxide and caesium hydroxide.

14. The process according to claim 2, wherein said at least one base is selected from the group consisting of potassium hydroxide, sodium hydroxide, lithium hydroxide, rubidium hydroxide and caesium hydroxide.

15. The process according to claim 6, wherein bringing the caesium and/or rubidium hydroxide into contact with at least one phenol substituted in position 4 of formula (I) is in an aqueous solution.

16. The process according to claim 6, further comprising an additional step of purifying said p-(R-oxy)calixarene or said mixture in the neutralized form.

17. The process according to claim 16, wherein said additional step of purifying is by crystallization from a mixture of solvents based on DMSO in order to obtain said p-(R-oxy) calixarene or said mixture in the purified neutralized form.

18. The process according to claim 8, wherein purifying is carried out by crystallization from a mixture of solvents based on DMSO to obtain
- said p-(R-oxy)calixarene or said mixture, substantially devoid of p-(R-oxy)calix[7]arene, in the neutralized form, or
- said p-(R-oxy)calixarene or said mixture, in combination with p-(R-oxy)calix[7]arene, in the neutralized form.

19. The phenolic dimer according to claim 9, wherein R is a benzyl group or an octyl group.

20. The p-(R-oxy)calix[n]arene or mixture of at least two p-(R-oxy)calix[n]arenes according to claim 10, wherein R is a benzyl group or an octyl group.

21. The p-(R-oxy)calix[n]arene or mixture of at least two p-(R-oxy)calix[n]arenes according to claim 10, wherein said p-(R-oxy)calixarene or said mixture of p-(R-oxy)calixarenes is in combination with p-(R-oxy)calix[7]arene.

22. The p-(R-oxy)calix[n]arene or mixture of at least two p-(R-oxy)calix[n]arenes according to claim 21, wherein said p-(R-oxy)calix[7]arene is in the form of the sodium or potassium monosalt.

23. The method according to claim 11, wherein said p-(R-oxy)calixarene or said mixture is in combination with p-(R-oxy)calix[7]arene.

24. The method according to claim 12, wherein R is a benzyl group or an octyl group.

25. The method according to claim 12, wherein said p-(R-oxy)calixarene or said mixture of p-(R-oxy)calixarenes is in combination with p-(R-oxy)calix[7]arene.

26. The method according to claim 25, wherein said p-(R-oxy)calix[7]arene is in the form of the sodium or potassium monosalt.

* * * * *